(12) United States Patent  
Maruo et al.

(10) Patent No.: US 7,976,781 B2
(45) Date of Patent: Jul. 12, 2011

(54) OZONE DETECTING DEVICE

(75) Inventors: Yasuko Maruo, Kanagawa (JP);
Takashi Miwa, Kanagawa (JP); Jiro Nakamura, Kanagawa (JP); Tatsuya Kunioka, Kanagawa (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 216 days.

(21) Appl. No.: 12/440,214

(22) PCT Filed: Oct. 2, 2007

(86) PCT No.: PCT/JP2007/069309
§ 371 (c)(1),
(2), (4) Date: Mar. 5, 2009

(87) PCT Pub. No.: WO2008/041712
PCT Pub. Date: Apr. 10, 2008

(65) Prior Publication Data
US 2010/0183480 A1    Jul. 22, 2010

(30) Foreign Application Priority Data
Oct. 2, 2006   (JP) ................................. 2006-270622
Feb. 20, 2007   (JP) ................................. 2007-039466

(51) Int. Cl.
*G01J 1/48*   (2006.01)
(52) U.S. Cl. .............................. 422/86; 422/87; 436/135
(58) Field of Classification Search ................ 422/56, 422/86, 87; 436/135
See application file for complete search history.

(56) References Cited

U.S. PATENT DOCUMENTS

| | | |
|---|---|---|
| 6,117,685 A * | 9/2000 | Omatsu et al. ............... 436/135 |
| 6,852,281 B2 * | 2/2005 | Inoue et al. .................... 422/58 |
| 7,662,636 B2 * | 2/2010 | Maruo et al. ................. 436/135 |
| 2004/0229372 A1 * | 11/2004 | Omatsu et al. ............... 436/135 |

FOREIGN PATENT DOCUMENTS

| | | |
|---|---|---|
| EP | 1163913 A | 12/2001 |
| JP | 07-012733 | * 1/1995 |
| JP | 09-318614 A | 12/1997 |

(Continued)

OTHER PUBLICATIONS

Baijnath, Y., et al., "A Photometric Method for Ozone Determination Using Alizarin Violet", J. Environ. Sci. Health Part A, 2004, vol. A 39, No. 9, pp. 2485-2492.

(Continued)

*Primary Examiner* — Jill Warden
*Assistant Examiner* — Monique Cole
(74) *Attorney, Agent, or Firm* — Blakely, Sokoloff, Taylor & Zafman

(57) ABSTRACT

An aqueous solution is formed by dissolving a dye made of alizarin and a humectant made of glycerin, and alkalized by dissolving a base (alkaline substance), thereby preparing a detector solution (101) in which the content of the humectant is about 20 wt %. An impregnated carrier (104) impregnated with the detector solution (101) is formed by dipping for 30 sec a sheet-like carrier (103) made of cellulose filter paper in the detector solution (101) so that the carrier (103) is impregnated with the detector solution (101). The impregnated carrier (104) is pulled up from the detector solution (101), and dried in dry nitrogen by evaporating a solvent such as water contained in the impregnated carrier (104), thereby forming an ozone detecting device (105).

10 Claims, 7 Drawing Sheets

FOREIGN PATENT DOCUMENTS

| | | |
|---|---|---|
| JP | 2000-111541 A | 4/2000 |
| JP | 2004-144729 A | 5/2004 |
| JP | 2005-003673 A | 1/2005 |

OTHER PUBLICATIONS

Franklin, et al., "Ozone Measurement in South Carolina Using Passive Sampler", Journal of the Air & Waste Measurement Association vol. 54, pp. 1312-1320, 2004.

"Operating Instructions for Ozone Monitor", Part#380010-10, http://www.kandmenvironmental.com/PDFs/ozone.pdf.

Maryadele J. O'Neil et al., "The Merck Index" An encyclopedia of chemicals, drugs, and biologicals, Thirteenth Edition, Published by Merck Research Laboratories Division of Merck & Co., Inc., 2001, p. 48, 246 Alizarin.

* cited by examiner

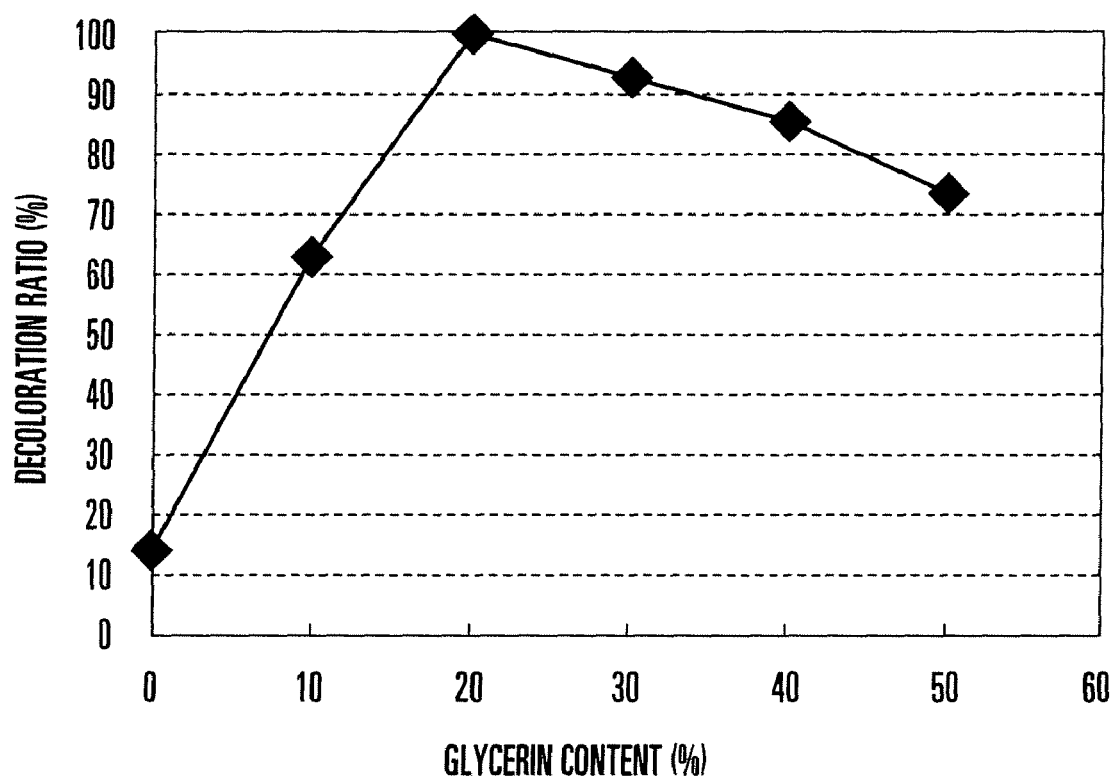
F I G. 2

OZONE DETECTING DEVICE

The present patent application is a non-provisional application of International Application No. PCT/JP2007/069309, filed Oct. 2, 2007.

TECHNICAL FIELD

The present invention relates to an ozone detecting device for detecting ozone existing in a gas such as the air by a discoloring reaction.

BACKGROUND ART

Presently, $NO_x$, SPM (Suspended Particulate Matter), and photochemical oxidant cause air pollution, and the influence on the environment is regarded as a problem. For example, the photochemical oxidant mainly containing a strongly acidic substance such as ozone is produced by a photochemical reaction caused by a pollutant such as $NO_x$ or hydrocarbon exhausted from factories, offices, and automobiles when the pollutant is irradiated with the sun light, and causes photochemical smog.

In Japan, environmental standards are set for these substances, and general environmental air measurement stations in various places measure the substances. For example, an environmental standard is set for the concentration of the photochemical oxidant, and general air environment observation stations in various places perform gas concentration measurements by an automatic measurement method such as an ultraviolet absorption method. Note that the environmental standard of the photochemical oxidant is 0.06 ppm or less as an average value measured per hour.

The ozone gas concentration measurement performed by the automatic measurement method described above measures ozone in the air by using a method of bubbling a gas to be measured in a neutral potassium iodide solution, and detecting the concentration by using a color developing reaction of generated iodine, or a method of detecting the concentration by using absorption of ozone in the ultraviolet region. Although these measurement methods can measure a slight amount of a gas, i.e., a few ppb of a gas, they have drawbacks that apparatuses are enlarged, complicated, and incapable of simple measurements. Also, these apparatuses are expensive and require constant setup in order to maintain the accuracy. In addition, automatic measurements performed by these apparatuses always require electric power and also require periodic calibration (maintenance). Therefore, enormous costs are required to maintain these apparatuses, and power supplies, temperature-controlled installation environments, and standard gases must be secured. That is, these apparatuses impose many limitations.

To accurately investigate the gas concentration distribution in an environment, evaluate the influence on a local environment, and evaluate the influence of exposure to a human body, an individual must monitor the environment by using a readily portable measurement method. For this purpose, the large-scale measurement apparatuses as described above cannot be used, and demands have arisen for the development of a an inexpensive, compact, and readily usable measurement device such as a gas sensor and a simple measurement method.

Recently, ozone is attracting attention because it has strong sterilizing power (oxidizing power), and changes into oxygen and produces no harmful substance after decomposition. This is extending the use of ozone to various industrial fields such as water processing, food sterilization, and paper bleaching. Accordingly, reference values of 100 ppb and 8 hrs are set for the ozone concentration as labor environmental standards. In a factory using ozone, it is of course necessary to install ozone alarms, and it is also necessary to manage the state in which each worker works within the range of the labor standards. This requires a measurement device that can be carried by a worker.

Under these circumstances, ozone gas measurement techniques have been presently extensively developed. Examples are a semiconductor gas sensor, solid-state electrolyte gas sensor, electrochemical gas sensor, and quartz oscillating gas sensor. However, these sensors have been developed to evaluate short-time responses, and only few sensors have been developed for monitoring requiring measurement data accumulation. When it is necessary to accumulate measurement data, therefore, the sensors must always be operated. Also, a sensing unit of, e.g., the semiconductor sensor must be held at a few hundred ° C., so a large amount of electric power is always necessary to constantly operate the sensor.

Furthermore, the above-mentioned sensors have a sensitivity of about sub-ppm, and hence cannot measure concentrations in real environments, e.g., cannot measure 10 ppb of ozone. Although some semiconductor sensors react to 10 ppb of ozone, the sensor output is nonlinear with respect to the concentration, and the output value largely changes from one sensor to another. This makes comparison difficult when using different sensors. Also, the influence of another gas cannot be neglected in many cases.

There is also a method using a detector tube type gas measurement device. Unfortunately, this method has also been developed to locally measure a very-short-time concentration in a measurement point. This makes it difficult to use the method to accumulate measurement data.

In addition to the above-mentioned ozone gas analyzing techniques, ozone detecting paper carrying (having) starch and potassium iodide (attached) has been proposed as a simple, high-sensitivity ozone analyzing technique (reference 1: Japanese Patent No. 3257622). However, this technique disclosed in patent reference 1 requires a pump for forcedly drawing a gas to be detected, a light source for measurement, and electric power for driving a detector including the pump and light source. Also, a special sheet-like carrier (substrate) is necessary, and must be replaced whenever measurement is performed. This makes cumulative measurement difficult. In addition, the measurement using the detecting paper described above detects all photochemical oxidants instead of ozone. Furthermore, this method has problems in accuracy and reproducibility because produced iodine gradually evaporates.

As another simple, high-sensitivity ozone gas analyzing method, a technique using ozone detecting paper carrying indigo carmine has been proposed (reference 2: Anna C. Franklin, et al., "Ozone Measurement in South Carolina Using Passive Sampler", Journal of the Air & Waste Measurement Association, Vol. 54, pp. 1312-1320, 2004). However, this ozone detecting paper has no sufficient sensitivity and cannot well measure a storage amount of 100 ppb×8 hrs as the labor environmental standard. A technique by which a membrane filter is placed on the surface of an ozone detecting sheet carrying a blue indigo dye, and the sensitivity is controlled by adjusting the thickness of the membrane filter has also been proposed (reference 3: "Operating Instructions for Ozone Monitor", Part#380010-10, http://www.kandmenvironmental.com/PDFs/ozone.pdf).

Furthermore, as a simple, advanced ozone detecting device, the present inventors have proposed an ozone detecting device using porous glass containing, in pores, a dye that changes light absorption in the visible region by reacting with ozone (reference 4: Japanese Patent Laid-Open No. 2004-144729). This technique can measure ozone gas at high accuracy without any large-scale apparatus. However, even this technique requires electric power to drive a light source and detector during measurement, and also requires an expensive carrier, i.e., porous glass.

DISCLOSURE OF INVENTION

Problems to be Solved by the Invention

As has been explained above, when accurately measuring ozone gas on the ppb order in accordance with the environmental standards, the conventional methods require expensive, large-scale apparatuses and much labor, and hence cannot easily measure ozone gas. Also, when performing simple measurement, the conventional techniques cannot easily measure storage amounts, and require electric power and special carriers. Accordingly, there is no readily portable measurement device easily usable by an individual.

The present invention has been made to solve the above problems, and has as its object to make it possible to simply detect the cumulative amount of ozone in a gas to be measured.

Means for Solving the Problems

An ozone detecting device according to the present invention at least includes a carrier made of fibers, a dye carried by the carrier, and an alkaline substance carried by the carrier, wherein the dye is selected from the group consisting of an anthraquinone-based dye having a hydroxy group, and an azo dye having a hydroxy group and a sulfurous acid group bonded to a position not adjacent to an azo group, and the alkaline substance is a substance which alkalizes an aqueous solution when dissolved. Accordingly, when the dye carried by the carrier reacts with ozone, the color of the ozone detecting device resulting from the dye changes.

Effect of the Invention

In the present invention as explained above, the carrier carries the alkaline substance in addition to the dye selected from the anthraquinone-based dye having a hydroxy group, and the azo dye having a hydroxy group and a sulfurous acid group bonded to a position not adjacent to an azo group. Consequently, the present invention achieves a remarkable effect of simply detecting the cumulative amount of ozone in a gas to be measured.

BRIEF DESCRIPTION OF DRAWINGS

FIG. 2 is a graph plotting the relationship between the difference between the light reflectances of an ozone detecting sheet using alizarin as an anthraquinone-based dye measured before and after exposure under exposure conditions of 0.1 ppm×5 hrs, and the content of glycerin in a detector solution;

BEST MODE FOR CARRYING OUT THE INVENTION

Embodiments of the present invention will be explained below with reference to the accompanying drawings.

Embodiment 1

Figure 1A:
FIGS. 1A to 1E are views of steps for explaining an example of an ozone detecting device manufacturing method according to Embodiment 1 of the present invention.

First, Embodiment 1 of the present invention will be explained. FIGS. 1A to 1E are views of steps for explaining an example of an ozone detecting device manufacturing method according to Embodiment 1 of the present invention. First, as shown in FIG. 1A, a vessel 102 containing a detector solution 101 is prepared. The detector solution 101 is an aqueous solution prepared by dissolving a dye made of alizarin (1,2-dihydroxyanthraquinone: $C_{14}H_8O_2(OH)_2$) and a humectant made of glycerin ($C_3H_8O_3$), and alkalized by dissolving a base. The content of the humectant is about 20 wt %.

For example, the detector solution 101 is prepared by dissolving 0.025 g of alizarin in 25 ml of an aqueous solution in which sodium hydroxide as a base that is an alkaline substance is dissolved at a concentration of 0.1 mol/liter, and adding 10 g of glycerin and water to the solution such that the total amount is 50 g. Alizarin is an anthraquinone-based dye (dyestuff). The detector solution 101 prepared by dissolving alizarin in an alkalized solution is a purple aqueous solution. The color of the detector solution 101 can be visually confirmed.

Figure 1B:

Then, as shown in FIG. 1B, a sheet-like carrier 103 having predetermined dimensions is prepared. The carrier 103 is a sheet made of fibers such as cellulose. An example is cellulose filter paper (No. 2) manufactured by ADVANTEC (TOYO FILTER PAPER). The color of the carrier 103 can be, e.g., white. Note that the carrier 103 is not limited to a sheet and may also have another shape. For example, the carrier 103 may also be a plate. As will be described later, the carrier 103 need only be a material made of fibers and capable of carrying the above-mentioned dye and an alkaline substance to be described later by impregnating the material with the detector solution 101. However, the carrier 103 having a sheet-like shape is more favorable from the viewpoints of detector solution impregnation to be described below and ozone detection.

Figure 1C:
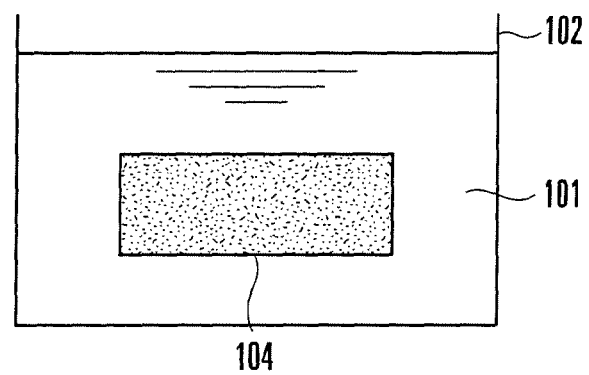

Subsequently, the prepared carrier 103 is dipped in the detector solution 101 for, e.g., 30 sec so as to impregnate the carrier 103 with the detector solution 101, thereby forming an impregnated carrier 104 impregnated with the detector solution 101 as shown in FIG. 1C. In this state, the impregnated carrier 104 is dyed by alizarin as a dyestuff.

Figure 1D:
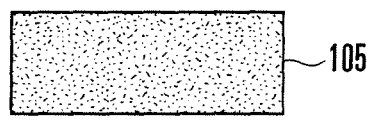
Figure 1E:
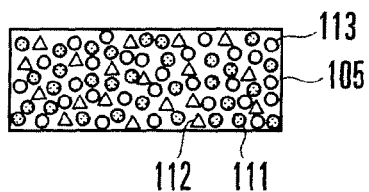

After that, the impregnated carrier 104 is pulled up from the detector solution 101, and dried in dry nitrogen by evaporating the solvent (medium) such as water contained in the impregnated carrier 104, thereby forming an ozone detecting device 105 as shown in FIG. 1D. As exemplarily shown in FIG. 1E, the ozone detecting device 105 thus formed carries alizarin as an anthraquinone-based dye having a hydroxy group as a dye 111, together with sodium hydroxide as an alkaline substance 112. The ozone detecting device 105 also carries glycerin as a humectant 113. The obtained ozone detecting device 105 is purple (dyed to be purple), and this color can be visually confirmed. Note that "carry" mentioned above indicates the state in which substances such as a dye, alkaline substance, and humectant chemically, physically, or electrically combine with a carrier (substrate), e.g., the state in which a sheet made of fibers such as cellulose is coated and/or impregnated with a dye.

When the ozone detecting device 105 manufactured as described above is exposed to an environment in which ozone exists, the concentration of purple gradually decreases with the elapse of the exposure time, and the color finally changes to white. For example, the color changes to white (returns to the original color of the filter paper) when the ozone detecting device 105 is exposed to an environment in which the ozone concentration is 0.04 ppm for 24 hrs. This color change is presumably discoloration corresponding to decomposition of alizarin as an anthraquinone-based dye by ozone.

Thus, the ozone detecting device 105 according to the present invention is capable of detecting ozone by the color change, and also capable of cumulative detection. The above-mentioned color change can be visually confirmed, so the ozone detecting device 105 can simply detect the cumulative amount of ozone. Also, the sheet-like carrier allows an individual to easily carry the device. As described above, the ozone detecting device of the present invention can very simply measure ozone without any large-scale apparatus, electric power, and special carrier.

A usable dye is not limited to alizarin, and it is possible to use an anthraquinone-based dye (dyestuff) having a hydroxy (—OH) group bonded to a benzene ring (anthracene). An example is Alizarin Red S (9,10-dihydro-3,4-dihydroxy-9, 10-dioxo-2-anthracenesulfonic acid, sodium salt: $C_{14}H_5O_2(OH)_2SO_3Na$). This anthraquinone-based dye causes the color change (discoloration) described above probably because ozone decomposes the quinone ring to change the dye molecular structure and electron state, and this changes light absorption in the visible region, thereby changing the color (hue).

Also, when the dye is alkalized by using sodium hydroxide or the like, hydrogen of the hydroxy group bonded to the benzene ring is eliminated, and an —$O^-$ group bonded to the benzene ring (anthracene) exists. When the —$O^-$ group bonded to the benzene ring thus exists, ozone is readily entrapped in (attracted to) this portion. This perhaps allows an easy reaction between the dye and ozone. As a consequence, ozone can be detected by using the anthraquinone-based dye having the hydroxy group bonded to the benzene ring.

The ozone detecting device 105 obtained by the manufacturing method shown in FIGS. 1A to 1E is formed by impregnation with the detector solution 101 containing about 20 wt % of the humectant. This more effectively exhibits the color change (ozone detecting capability) caused by the existence of ozone. That is, the reaction between the dye and ozone in the ozone detecting device 105 is presumably accelerated because the humectant is contained (carried). However, if the concentration of the humectant in the detector solution is too high, e.g., exceeds 50%, the time required for drying becomes enormous. This makes it difficult to manufacture a detecting device having high reproducibility.

The relationship between the amount of humectant and the color change of the ozone detecting device caused by the existence of ozone will be explained below. That is, the comparison of a plurality of samples (ozone detecting devices) manufactured by changing the humectant amount (content) in the detector solution 101 will be explained.

First, 0.025 g of alizarin are dissolved in 25 ml of an aqueous 0.1-mol/liter sodium hydroxide solution, and water is added to the solution such that the total amount is 50 g, thereby preparing (forming) detector solution A. The formed detector solution does not contain glycerin as a humectant. Ozone detecting device A is formed by using detector solution A in the same manner as described above. The color of ozone detecting device A thus formed is purple.

Also, 0.025 g of alizarin are dissolved in 25 ml of an aqueous 0.1-mol/liter sodium hydroxide solution, and 5 g of glycerin as a humectant and water are added to the solution to make 50 g, thereby forming detector solution B. Ozone detecting device B is formed by using detector solution B in the same manner as described above. The color of ozone detecting device B thus formed is purple.

In addition, 0.025 g of alizarin are dissolved in 25 ml of an aqueous 0.1-mol/liter sodium hydroxide solution, and 10 g of glycerin as a humectant and water are added to the solution to make 50 g, thereby forming detector solution C. Ozone detecting device C is formed by using detector solution C in the same manner as described above. The color of ozone detecting device C thus formed is purple.

Likewise, 0.025 g of alizarin are dissolved in 25 ml of an aqueous 0.1-mol/liter sodium hydroxide solution, and 15 g of glycerin as a humectant and water are added to the solution such that the total amount is 50 g, thereby forming detector solution D. Ozone detecting device D is formed by using detector solution D in the same manner as described above. The color of ozone detecting device D thus formed is purple.

Also, 0.025 g of alizarin are dissolved in 25 ml of an aqueous 0.1-mol/liter sodium hydroxide solution, and 20 g of glycerin as a humectant and water are added to the solution such that the total amount is 50 g, thereby forming detector solution E. Ozone detecting device E is formed by using detector solution E in the same manner as described above. The color of ozone detecting device E thus formed is purple.

Furthermore, 0.025 g of alizarin are dissolved in 25 ml of an aqueous 0.1-mol/liter sodium hydroxide solution, and 25 g of glycerin as a humectant and water are added to the solution such that the total amount is 50 g, thereby forming detector solution F. Ozone detecting device F is formed by using detector solution F in the same manner as described above. The color of ozone detecting device F thus formed is purple.

Under the conditions shown in Table 1 below, each of the samples (ozone detecting devices A, B, C, D, E, and F) described above was placed in a box filled with ozone at a predetermined concentration and exposed to the ozone gas at 25° C. and a humidity of 60%, and the discoloration properties were observed with the naked eye. Note that the volume of the box is 200 liters, and, in order to analyze the internal ozone concentration, the internal air is exhausted at a rate of 2 liters/min, and air containing ozone at a predetermined concentration is supplied at a rate of 2 liters/min. Each ozone detecting device is thus exposed to the air as a detection object, and the color change of the device is visually observed.

In this color change observation, a color chart on which the light absorption intensity at a wavelength of about 500 to 600 nm at which alkalized alizarin absorbs light changes by five steps is prepared, and the color change of each ozone detecting device is compared with this color chart and evaluated by the five steps. In this evaluation, an evaluation result "1" indicates the state in which no color change is observed. Evaluation results "2", "3", and "4" indicate that the concentration of purple decreases in this order. An evaluation result "5" indicates the state in which the changed color of the ozone detecting device is white because the color of alizarin is faded. Also, if the observed color exists between the individual steps in comparison with the four-step color chart, e.g., if the observed color exists between "2" and "3", the evaluation result is "2.5".

TABLE 1

| | Cumulative amount | A | B | C | D | E | F |
|---|---|---|---|---|---|---|---|
| 0.04 ppm × 5 hrs discoloration properties | 0.2 | 1 | 2 | 2.5 | 2.5 | 2 | 2 |
| 0.075 ppm × 5 hrs discoloration properties | 0.375 | 1 | 3 | 4 | 4 | 3.5 | 3 |
| 0.1 ppm × 5 hrs discoloration properties | 0.5 | 1 | 3.5 | 5 | 4.5 | 4 | 4 |
| 0.04 ppm × 24 hrs discoloration properties | 0.96 | 2 | 4 | 5 | 5 | 5 | 5 |
| 0.075 ppm × 24 hrs discoloration properties | 1.8 | 3 | 5 | 5 | 5 | 5 | 5 |

The results shown in Table 1 reveal that detecting devices B to F containing the humectant can reliably detect ozone by cumulation of five-hour exposure even when the ozone concentration is as low as 0.04 ppm. In addition, it is obviously possible to distinguish between the colors when the device is exposed to 0.04 ppm for 5 hrs and 0.075 ppm for 5 hrs. When an individual carries the device for one day, therefore, an approximate exposure amount can be estimated from the color.

FIG. 2 is a graph plotting the relationship between the difference between the light reflectances measured before and after exposure under exposure conditions of 0.1 ppm×5 hrs, and the content of glycerin in the detector solution. The light reflectance was measured using a Hitachi spectrophotometer having a reflecting unit. Note that FIG. 2 shows the change in light reflectance as the ratio of decoloration. The result shown in FIG. 2 demonstrates that the amount of humectant (glycerin) in the detector solution used when forming the ozone detecting device changes the reflectance change amount per unit time when exposing the formed ozone detecting device to ozone.

When the content of glycerin as a humectant is 20% or less, the reflectance change amount per unit time increases as the glycerin content increases. Note that the color change can be visually confirmed when the decoloration ratio is 30% or more. Therefore, a favorable glycerin content in the detector solution for forming the ozone detecting device is probably 3% to 50%. When detecting high-concentration ozone on a 10-ppm level, however, the glycerin content is preferably 3% or less (including zero glycerin) in some cases.

Embodiment 2

Another ozone detecting device according to Embodiment 2 of the present invention will be explained below. In this embodiment, the case in which Alizarin Red S (also called Mordant Red 3) was used as an anthraquinone-based dye instead of alizarin described above will be explained. First, 0.03 g of Alizarin Red S are dissolved in 25 ml of an aqueous 0.1-mol/liter sodium hydroxide solution, and water is added to the solution such that the total amount is 50 g, thereby forming detector solution G. The formed detector solution does not contain glycerin as a humectant. Ozone detecting device G is formed by using detector solution G in the same manner as described above. The color of ozone detecting device G thus formed is purple.

Also, 0.03 g of Alizarin Red S are dissolved in 25 ml of an aqueous 0.1-mol/liter sodium hydroxide solution, and 5 g of glycerin as a humectant and water are added to the solution to make 50 g, thereby forming detector solution H. Ozone detecting device H is formed by using detector solution H in the same manner as described above. The color of ozone detecting device H thus formed is purple.

In addition, 0.03 g of Alizarin Red S are dissolved in 25 ml of an aqueous 0.1-mol/liter sodium hydroxide solution, and 10 g of glycerin as a humectant and water are added to the solution to make 50 g, thereby forming detector solution I. Ozone detecting device I is formed by using detector solution I in the same manner as described above. The color of ozone detecting device I thus formed is purple.

Likewise, 0.03 g of Alizarin Red S are dissolved in 25 ml of an aqueous 0.1-mol/liter sodium hydroxide solution, and 15 g of glycerin as a humectant and water are added to the solution to make 50 g, thereby forming detector solution J. Ozone detecting device J is formed by using detector solution J in the same manner as described above. The color of ozone detecting device J thus formed is purple.

Also, 0.03 g of Alizarin Red S are dissolved in 25 ml of an aqueous 0.1-mol/liter sodium hydroxide solution, and 20 g of glycerin as a humectant and water are added to the solution to make 50 g, thereby forming detector solution K. Ozone detecting device K is formed by using detector solution K in the same manner as described above. The color of ozone detecting device K thus formed is purple.

Furthermore, 0.03 g of Alizarin Red S are dissolved in 25 ml of an aqueous 0.1-mol/liter sodium hydroxide solution, and 25 g of glycerin as a humectant and water are added to the solution to make 50 g, thereby forming detector solution L. Ozone detecting device L is formed by using detector solution L in the same manner as described above. The color of ozone detecting device L thus formed is purple.

Under the conditions shown in Table 2 below, each of ozone detecting devices G to L thus formed was placed in a box filled with ozone at a predetermined concentration and exposed to the ozone gas at 25° C. and a humidity of 60%, and the discoloration properties were observed with the naked eye. The volume of the box is 200 liters, and, in order to analyze the internal ozone concentration, the internal air is exhausted at a rate of 2 liters/min, and air containing ozone at a predetermined concentration is supplied at a rate of 2 liters/min. In color change observation, a color chart on which the light absorption intensity at a wavelength of 500 to 600 nm at which alkalized Alizarin Red S absorbs light changed by five steps was prepared, and the color change of each ozone detecting device was compared with this color chart and evaluated by the five steps. This color chart is based on the color colored (dyed) by Alizarin Red S.

TABLE 2

| | Cumulative amount | G | H | I | J | K | L |
|---|---|---|---|---|---|---|---|
| 0.04 ppm × 5 hrs discoloration properties | 0.2 | 1 | 1 | 2 | 1.5 | 1 | 1 |
| 0.075 ppm × 5 hrs discoloration properties | 0.375 | 1 | 1.5 | 2.5 | 2 | 1.5 | 1.5 |
| 0.1 ppm × 5 hrs discoloration properties | 0.5 | 1 | 2 | 3 | 2.5 | 2 | 1.5 |

TABLE 2-continued

| | Cumulative amount | G | H | I | J | K | L |
|---|---|---|---|---|---|---|---|
| 0.04 ppm × 24 hrs discoloration properties | 0.96 | 1 | 2.5 | 5 | 4 | 2.5 | 2 |
| 0.075 ppm × 24 hrs discoloration properties | 1.8 | 1 | 4 | 5 | 5 | 4 | 3.5 |

In this evaluation, an evaluation result "1" indicates the state in which no color change is observed. Evaluation results "2", "3", and "4" indicate that the concentration of the color of Alizarin Red S decreases in this order. An evaluation result "5" indicates the state in which the changed color of the ozone detecting device is not the color of Alizarin Red S but white because the color of Alizarin Red S is faded. Also, if the observed color exists between the individual steps in comparison with the color chart, e.g., if the observed color exists between "2" and "3", the evaluation result is "2.5".

The results shown in Table 2 reveal that detecting devices I and J can reliably detect ozone by cumulation of five-hour exposure even when the ozone concentration is as low as 0.04 ppm. In addition, it is obviously possible to distinguish between the colors in each of ozone detecting devices H to L when the device is exposed to 0.04 ppm for 5 hrs and 0.075 ppm for 5 hrs. When an individual carries the device for one day, therefore, an approximate exposure amount can be estimated from the color.

Note that glycerin is used as a humectant in the embodiments described above, but the present invention is not limited to this, and it is also possible to use, e.g., ethyleneglycol or propyleneglycol as will be described below. Note also that another humectant in which the above-mentioned dyes dissolve may also be used.

Comparative examples in which detecting devices were formed as they were not alkalized will be explained below. In the following comparative examples, ozone detecting devices using sheet-like filter paper as a carrier will be explained.

Comparative Example 1

First, the case in which alizarin as the same anthraquinone-based dye as that used in Embodiment 1 was used without being alkalized will be explained. First, 0.025 g of alizarin are dissolved in 20 ml of ethanol, and water is added to the solution such that the total amount is 50 g, thereby preparing (forming) detector solution A-1. The formed detector solution does not contain glycerin as a humectant. Ozone detecting device A-1 is formed in the same manner as described above by using detector solution A-1. The color of ozone detecting device A-1 thus formed is yellow.

The formation of ozone detecting device A-1 will be briefly explained below. First, a sheet-like carrier having predetermined dimensions is dipped in formed detector solution A-1 for about 30 sec so that the carrier is impregnated with detector solution A-1, and the impregnated carrier is dried (with air). As the carrier, it is possible to use, e.g., cellulose filter paper (No. 2) manufactured by ADVANTEC (TOYO FILTER PAPER). The color of ozone detecting device A-1 thus formed is yellow (dyed to be yellow), and this color can be visually confirmed.

Also, 0.025 g of alizarin are dissolved in 20 ml of ethanol, and 5 g of glycerin as a humectant and water are added to the solution to make 50 g, thereby forming detector solution B-1. Ozone detecting device B-1 is formed in the same manner as described above by using detector solution B-1. The color of ozone detecting device B-1 thus formed is yellow.

Additionally, 0.025 g of alizarin are dissolved in 20 ml of ethanol, and 10 g of glycerin as a humectant and water are added to the solution to make 50 g, thereby forming detector solution C-1. Ozone detecting device C-1 is formed in the same manner as described above by using detector solution C-1. The color of ozone detecting device C-1 thus formed is yellow.

Similarly, 0.025 g of alizarin are dissolved in 20 ml of ethanol, and 15 g of glycerin as a humectant and water are added to the solution to make 50 g, thereby forming detector solution D-1. Ozone detecting device D-1 is formed in the same manner as described above by using detector solution D-1. The color of ozone detecting device D-1 thus formed is yellow.

Also, 0.025 g of alizarin are dissolved in 20 ml of ethanol, and 20 g of glycerin as a humectant and water are added to the solution to make 50 g, thereby forming detector solution E-1. Ozone detecting device E-1 is formed in the same manner as described above by using detector solution E-1. The color of ozone detecting device E-1 thus formed is yellow.

Furthermore, 0.025 g of alizarin are dissolved in 20 ml of ethanol, and 25 g of glycerin as a humectant and water are added to the solution to make 50 g, thereby forming detector solution F-1. Ozone detecting device F-1 is formed in the same manner as described above by using detector solution F-1. The color of ozone detecting device F-1 thus formed is yellow.

Under the conditions shown in Table 3 below, each of ozone detecting devices A-1 to F-1 thus formed was placed in a box filled with ozone at a predetermined concentration and exposed to the ozone gas at 25° C. and a humidity of 60%, and the discoloration properties were observed with the naked eye. The volume of the box is 200 liters, and, in order to analyze the internal ozone concentration, the internal air is exhausted at a rate of 2 liters/min, and air containing ozone at a predetermined concentration is supplied at a rate of 2 liters/min.

TABLE 3

| | Cumulative amount | A-1 | B-1 | C-1 | D-1 | E-1 | F-1 |
|---|---|---|---|---|---|---|---|
| 0.04 ppm × 5 hrs discoloration properties | 0.2 | 1 | 1 | 1 | 1 | 1 | 1 |
| 0.075 ppm × 5 hrs discoloration properties | 0.375 | 1 | 1 | 1 | 1 | 1 | 1 |
| 0.1 ppm × 5 hrs discoloration properties | 0.5 | 1 | 1 | 1 | 1 | 1 | 1 |
| 0.04 ppm × 24 hrs discoloration properties | 0.96 | 1 | 1 | 1 | 1 | 1 | 1 |
| 0.075 ppm × 24 hrs discoloration properties | 1.8 | 1 | 1.5 | 1.5 | 1.5 | 1.5 | 1 |

In color change observation, a yellow color chart on which the light absorption intensity at a wavelength of 450 nm at which neutralized alizarin absorbs light changed by five steps was prepared, and the color change of each ozone detecting device was compared with this color chart and evaluated by the five steps. In this evaluation, an evaluation result "1" indicates the state in which no color change is observed.

Evaluation results "2", "3", and "4" indicate that the concentration of the color of alizarin decreases in this order. An evaluation result "5" indicates the state in which the changed color of the ozone detecting device is not the color of alizarin but white because the color of alizarin is faded. Also, if the observed color exists between the individual steps in comparison with the color chart, e.g., if the observed color exists between "2" and "3", the evaluation result is "2.5".

The results shown in Table 3 reveal that when using neutralized alizarin, slight color changes were observed under conditions of 0.075 ppm and 24 hrs by which the ozone exposure amount was largest, but no color fading was observed under other conditions. Thus, a detecting device using neutralized alizarin as an anthraquinone-based dyestuff cannot simply detect ozone at a low concentration of 0.1 ppm or less.

Comparative Example 2

The case in which Alizarin Red S as another anthraquinone-based dye is used will be explained below. In the following explanation, an ozone detecting device using sheet-like filter paper as a carrier will be described as an example. First, 0.033 g of Alizarin Red S are dissolved in 20 ml of ethanol, and water is added to the solution to make 50 g, thereby forming detector solution G-1. Detector solution G-1 thus formed does not contain glycerin as a humectant. Ozone detecting device G-1 is formed in the same manner as described above by using detector solution G-1. The color of ozone detecting device G-1 thus formed is yellow.

Also, 0.033 g of Alizarin Red S are dissolved in 20 ml of ethanol, and 5 g of glycerin as a humectant and water are added to the solution to make 50 g, thereby forming detector solution H-1. Ozone detecting device H-1 is formed in the same manner as described above by using detector solution H-1. The color of ozone detecting device H-1 thus formed is yellow.

In addition, 0.033 g of Alizarin Red S are dissolved in 20 ml of ethanol, and 10 g of glycerin as a humectant and water are added to the solution to make 50 g, thereby forming detector solution I-1. Ozone detecting device I-1 is formed in the same manner as described above by using detector solution I-1. The color of ozone detecting device I-1 thus formed is yellow.

Likewise, 0.033 g of Alizarin Red S are dissolved in 20 ml of ethanol, and 15 g of glycerin as a humectant and water are added to the solution to make 50 g, thereby forming detector solution J-1. Ozone detecting device J-1 is formed in the same manner as described above by using detector solution J-1. The color of ozone detecting device J-1 thus formed is yellow.

Also, 0.033 g of Alizarin Red S are dissolved in 20 ml of ethanol, and 20 g of glycerin as a humectant and water are added to the solution to make 50 g, thereby forming detector solution K-1. Ozone detecting device K-1 is formed in the same manner as described above by using detector solution K-1. The color of ozone detecting device K-1 thus formed is yellow.

Furthermore, 0.033 g of Alizarin Red S are dissolved in 20 ml of ethanol, and 25 g of glycerin as a humectant and water are added to the solution to make 50 g, thereby forming detector solution L-1. Ozone detecting device L-1 is formed in the same manner as described above by using detector solution L-1. The color of ozone detecting device L-1 thus formed is yellow.

Under the conditions shown in Table 4 below, each of ozone detecting devices G-1 to L-1 thus formed was placed in a box filled with ozone at a predetermined concentration and exposed to the ozone gas at 25° C. and a humidity of 60%, and the discoloration properties were observed with the naked eye. The volume of the box is 200 liters, and, in order to analyze the internal ozone concentration, the internal air is exhausted at a rate of 2 liters/min, and air containing ozone at a predetermined concentration is supplied at a rate of 2 liters/min.

TABLE 4

| | Cumulative amount | G-1 | H-1 | I-1 | J-1 | K-1 | L-1 |
|---|---|---|---|---|---|---|---|
| 0.04 ppm × 5 hrs discoloration properties | 0.2 | 1 | 1 | 1 | 1 | 1 | 1 |
| 0.075 ppm × 5 hrs discoloration properties | 0.375 | 1 | 1 | 1 | 1 | 1 | 1 |
| 0.1 ppm × 5 hrs discoloration properties | 0.5 | 1 | 1 | 1 | 1 | 1 | 1 |
| 0.04 ppm × 24 hrs discoloration properties | 0.96 | 1 | 1 | 1 | 1 | 1 | 1 |
| 0.075 ppm × 24 hrs discoloration properties | 1.8 | 1 | 1 | 1 | 1 | 1 | 1 |

In color change observation, a yellow (the color of Alizarin Red S) color chart on which the light absorption intensity at a wavelength of 450 nm at which unalkalized (neutral) Alizarin Red S absorbs light changed by five steps was prepared, and the color change of each ozone detecting device was compared with this color chart and evaluated by the five steps. In this evaluation, an evaluation result "1" indicates the state in which no color change is observed. Evaluation results "2", "3", and "4" indicate that the concentration of yellow decreases in this order. An evaluation result "5" indicates the state in which the changed color of the ozone detecting device is not yellow but white because the color of Alizarin Red S is faded. Also, if the observed color exists between the individual steps in comparison with the color chart, e.g., if the observed color exists between "2" and "3", the evaluation result is "2.5".

The results shown in Table 4 reveal that when using unalkalized Alizarin Red S, no color fading is observed in any ozone detecting devices (samples) under any exposure conditions. Thus, a detecting device using neutralized Alizarin Red S as an anthraquinone-based dyestuff cannot simply detect ozone at a low concentration of 0.1 ppm or less.

Comparative Example 3

The case in which alizarin as the same anthraquinone-based dye as that used in Embodiment 1 was used after being acidified will now be explained. First, 0.025 g of alizarin are dissolved in 40 ml of acetic acid, and water is added to the solution such that the total amount is 50 g, thereby preparing (forming) detector solution A-2. The formed detector solution does not contain glycerin as a humectant. Ozone detecting device A-2 is formed in the same manner as described above by using detector solution A-2. The color of ozone detecting device A-2 thus formed is reddish blown.

The formation of ozone detecting device A-2 will be briefly explained below. First, a carrier having predetermined dimensions is dipped in formed detector solution A-2 for about 30 sec so that the carrier is impregnated with detector solution A-2, and the impregnated carrier is dried (with air). As the carrier, it is possible to use, e.g., cellulose filter paper (No. 2)

manufactured by ADVANTEC (TOYO FILTER PAPER). The color of ozone detecting device A-2 thus formed is reddish blown (dyed to be reddish blown), and this color can be visually confirmed.

Also, 0.025 g of alizarin are dissolved in 40 ml of acetic acid, and 5 g of glycerin as a humectant and water are added to the solution to make 50 g, thereby forming detector solution B-2. Ozone detecting device B-2 is formed in the same manner as described above by using detector solution B-2. The color of ozone detecting device B-2 thus formed is reddish blown.

Additionally, 0.025 g of alizarin are dissolved in 40 ml of acetic acid, and 10 g of glycerin as a humectant and water are added to the solution to make 50 g, thereby forming detector solution C-2. Ozone detecting device C-2 is formed in the same manner as described above by using detector solution C-2. The color of ozone detecting device C-2 thus formed is reddish blown.

Under the conditions shown in Table 5 below, each of ozone detecting devices A-2 to C-2 thus formed was placed in a box filled with ozone at a predetermined concentration and exposed to the ozone gas at 25° C. and a humidity of 60%, and the discoloration properties were observed with the naked eye. The volume of the box is 200 liters, and, in order to analyze the internal ozone concentration, the internal air is exhausted at a rate of 2 liters/min, and air containing ozone at a predetermined concentration is supplied at a rate of 2 liters/min.

TABLE 5

| | Cumulative amount | A-2 | B-2 | C-2 |
|---|---|---|---|---|
| 0.04 ppm × 5 hrs discoloration properties | 0.2 | 1 | 1 | 1 |
| 0.075 ppm × 5 hrs discoloration properties | 0.375 | 1 | 1 | 1 |
| 0.1 ppm × 5 hrs discoloration properties | 0.5 | 1 | 1 | 1 |
| 0.04 ppm × 24 hrs discoloration properties | 0.96 | 1 | 1 | 1 |
| 0.075 ppm × 24 hrs discoloration properties | 1.8 | 1 | 1.5 | 1.5 |

In color change observation, a reddish blown color chart on which the light absorption intensity at a wavelength of 450 to 480 nm at which acidified alizarin absorbs light changed by five steps was prepared, and the color change of each ozone detecting device was compared with this color chart and evaluated by the five steps. In this evaluation, an evaluation result "1" indicates the state in which no color change is observed. Evaluation results "2", "3", and "4" indicate that the concentration of the color of acidified alizarin decreases in this order. An evaluation result "5" indicates the state in which the changed color of the ozone detecting device is not the color of acidified alizarin but white because the color of alizarin is faded. Also, if the observed color exists between the individual steps in comparison with the color chart, e.g., if the observed color exists between "2" and "3", the evaluation result is "2.5".

The results shown in Table 5 reveal that when using acidified alizarin, slight color changes were observed under conditions of 0.075 ppm and 24 hrs by which the ozone exposure amount was largest, but no color fading was observed under other conditions. Thus, a detecting device using acidified alizarin as an anthraquinone-based dyestuff cannot simply detect ozone at a low concentration of 0.1 ppm or less.

Embodiment 3

The case in which ethyleneglycol was used as a humectant will be explained below. First, 0.025 g of alizarin are dissolved in 25 ml of an aqueous 0.1-mol/liter sodium hydroxide solution, and 5 g of ethyleneglycol as a humectant and water are added to the solution to make 50 g, thereby forming detector solution M. Ozone detecting device M is formed by using detector solution M in the same manner as described above. The color of ozone detecting device M thus formed is purple.

Also, 0.025 g of alizarin are dissolved in 25 ml of an aqueous 0.1-mol/liter sodium hydroxide solution, and 10 g of ethyleneglycol as a humectant and water are added to the solution to make 50 g, thereby forming detector solution N. Ozone detecting device N is formed by using detector solution N in the same manner as described above. The color of ozone detecting device N thus formed is purple.

In addition, 0.025 g of alizarin are dissolved in 25 ml of an aqueous 0.1-mol/liter sodium hydroxide solution, and 15 g of ethyleneglycol as a humectant and water are added to the solution such that the total amount is 50 g, thereby forming detector solution O. Ozone detecting device O is formed by using detector solution O in the same manner as described above. The color of ozone detecting device O thus formed is purple.

Analogously, 0.025 g of alizarin are dissolved in 25 ml of an aqueous 0.1-mol/liter sodium hydroxide solution, and 20 g of ethyleneglycol as a humectant and water are added to the solution such that the total amount is 50 g, thereby forming detector solution P. Ozone detecting device P is formed by using detector solution P in the same manner as described above. The color of ozone detecting device P thus formed is purple.

Furthermore, 0.025 g of alizarin are dissolved in 25 ml of an aqueous 0.1-mol/liter sodium hydroxide solution, and 25 g of ethyleneglycol as a humectant and water are added to the solution such that the total amount is 50 g, thereby forming detector solution Q. Ozone detecting device Q is formed by using detector solution Q in the same manner as described above. The color of ozone detecting device Q thus formed is purple.

Under the conditions shown in Table 6 below, each of the samples (ozone detecting devices M, N, O, P, and Q) described above was placed in a box filled with ozone at a predetermined concentration and exposed to the ozone gas at 25° C. and a humidity of 60%, and the discoloration properties were observed with the naked eye. Note that the volume of the box is 200 liters, and, in order to analyze the internal ozone concentration, the internal air is exhausted at a rate of 2 liters/min, and air containing ozone at a predetermined concentration is supplied at a rate of 2 liters/min. Each ozone detecting device is thus exposed to the air as a detection object, and the color change of the device is visually observed.

In this color change observation, a color chart on which the light absorption intensity at a wavelength of about 500 to 600 nm at which alkalized alizarin absorbs light changes by five steps is prepared, and the color change of each ozone detecting device is compared with this color chart and evaluated by the five steps. In this evaluation, an evaluation result "1" indicates the state in which no color change is observed. Evaluation results "2", "3", and "4" indicate that the concentration of purple decreases in this order. An evaluation result "5" indicates the state in which the changed color of the ozone detecting device is white because the color of alizarin is faded. Also, if the observed color exists between the individual steps in comparison with the four-step color chart, e.g., if the observed color exists between "2" and "3", the evaluation result is "2.5".

TABLE 6

| | Cumulative amount | M | N | O | P | Q |
|---|---|---|---|---|---|---|
| 0.04 ppm × 5 hrs discoloration properties | 0.2 | 1.5 | 2 | 2.5 | 3 | 2.5 |
| 0.075 ppm × 5 hrs discoloration properties | 0.375 | 2 | 2.5 | 3.5 | 4 | 3.5 |
| 0.1 ppm × 5 hrs discoloration properties | 0.5 | 2.5 | 3 | 4 | 5 | 4.5 |
| 0.04 ppm × 24 hrs discoloration properties | 0.96 | 3.5 | 4 | 5 | 5 | 5 |
| 0.075 ppm × 24 hrs discoloration properties | 1.8 | 5 | 5 | 5 | 5 | 5 |

The results shown in Table 6 reveal that detecting devices M to Q containing the humectant can reliably detect ozone by five-hour cumulation even when the ozone concentration is as low as 0.04 ppm. In addition, it is obviously possible to distinguish between the colors when the device is exposed to 0.04 ppm for 5 hrs and 0.075 ppm for 5 hrs. When an individual carries the device for one day, therefore, an approximate exposure amount can be estimated from the color.

Embodiment 4

The case in which propyleneglycol was used as a humectant will be explained below. First, 0.025 g of alizarin are dissolved in 25 ml of an aqueous 0.1-mol/liter sodium hydroxide solution, and 5 g of propyleneglycol as a humectant and water are added to the solution to make 50 g, thereby forming detector solution R. Ozone detecting device R is formed by using detector solution R in the same manner as described above. The color of ozone detecting device R thus formed is purple.

Also, 0.025 g of alizarin are dissolved in 25 ml of an aqueous 0.1-mol/liter sodium hydroxide solution, and 10 g of propyleneglycol as a humectant and water are added to the solution to make 50 g, thereby forming detector solution S. Ozone detecting device S is formed by using detector solution S in the same manner as described above. The color of ozone detecting device S thus formed is purple.

Additionally, 0.025 g of alizarin are dissolved in 25 ml of an aqueous 0.1-mol/liter sodium hydroxide solution, and 15 g of propyleneglycol as a humectant and water are added to the solution such that the total amount is 50 g, thereby forming detector solution T. Ozone detecting device T is formed by using detector solution T in the same manner as described above. The color of ozone detecting device T thus formed is purple.

Likewise, 0.025 g of alizarin are dissolved in 25 ml of an aqueous 0.1-mol/liter sodium hydroxide solution, and 20 g of propyleneglycol as a humectant and water are added to the solution such that the total amount is 50 g, thereby forming detector solution U. Ozone detecting device U is formed by using detector solution U in the same manner as described above. The color of ozone detecting device U thus formed is purple.

Furthermore, 0.025 g of alizarin are dissolved in 25 ml of an aqueous 0.1-mol/liter sodium hydroxide solution, and 25 g of propyleneglycol as a humectant and water are added to the solution such that the total amount is 50 g, thereby forming detector solution V. Ozone detecting device V is formed by using detector solution V in the same manner as described above. The color of ozone detecting device V thus formed is purple.

Under the conditions shown in Table 7 below, each of the samples (ozone detecting devices R, S, T, U, and V) described above was placed in a box filled with ozone at a predetermined concentration and exposed to the ozone gas at 25° C. and a humidity of 60%, and the discoloration properties were observed with the naked eye. Note that the volume of the box is 200 liters, and, in order to analyze the internal ozone concentration, the internal air is exhausted at a rate of 2 liters/min, and air containing ozone at a predetermined concentration is supplied at a rate of 2 liters/min. Each ozone detecting device is thus exposed to the air as a detection object, and the color change of the device is visually observed.

In this color change observation, a color chart on which the light absorption intensity at a wavelength of about 500 to 600 nm at which alkalized alizarin absorbs light changes by five steps is prepared, and the color change of each ozone detecting device is compared with this color chart and evaluated by the five steps. In this evaluation, an evaluation result "1" indicates the state in which no color change is observed. Evaluation results "2", "3", and "4" indicate that the concentration of purple decreases in this order. An evaluation result "5" indicates the state in which the changed color of the ozone detecting device is white because the color of alizarin is faded. Also, if the observed color exists between the individual steps in comparison with the four-step color chart, e.g., if the observed color exists between "2" and "3", the evaluation result is "2.5".

TABLE 7

| | Cumulative amount | R | S | T | U | V |
|---|---|---|---|---|---|---|
| 0.04 ppm × 5 hrs discoloration properties | 0.2 | 1.5 | 2 | 2.5 | 3 | 2.5 |
| 0.075 ppm × 5 hrs discoloration properties | 0.375 | 2 | 2.5 | 3.5 | 4.5 | 3.5 |
| 0.1 ppm × 5 hrs discoloration properties | 0.5 | 2.5 | 3 | 4 | 5 | 4 |
| 0.04 ppm × 24 hrs discoloration properties | 0.96 | 3 | 3.5 | 4.5 | 5 | 4.5 |
| 0.075 ppm × 24 hrs discoloration properties | 1.8 | 5 | 5 | 5 | 5 | 5 |

The results shown in Table 7 reveal that detecting devices R to V containing the humectant can reliably detect ozone by five-hour cumulation even when the ozone concentration is as low as 0.04 ppm. In addition, it is obviously possible to distinguish between the colors when the device is exposed to 0.04 ppm for 5 hrs and 0.075 ppm for 5 hrs. When an individual carries the device for one day, therefore, an approximate exposure amount can be estimated from the color.

When using detecting devices using no humectant such as glycerin, it is difficult to visually confirm the color change as indicated by the experimental results of detecting device A shown in Table 1 and detecting device G shown in Table 2. Especially when using detecting device G using Alizarin Red S, no color change is visually confirmed within the range of the experiment. As described previously, the humectant presumably accelerates the reaction between the dye and ozone. When using no humectant, therefore, the reaction between the dye and ozone is not so accelerated, so no color change perhaps occurs within the range that can be visually confirmed. However, even when using no humectant such as glycerin, decoloration can be measured by using a higher-accuracy light measurement method such as reflection spectrophotometry.

For example, high-concentration ozone gas is used when performing sterilization by ozone, and this ozone gas must have a high concentration equal to or higher than a predetermined value. The high-sensitivity ozone detecting device 105 described earlier cannot detect the state of this high-concentration ozone gas. This is so because the color of a high-sensitivity ozone detecting device changes in response to even a concentration equal to or lower than the predetermined concentration. By contrast, the color of a low-sensitivity ozone detecting device using no humectant such as glycerin hardly changes in response to a concentration equal to or lower than the predetermined concentration, and hence is presumably applicable to detection of high-concentration ozone gas.

Embodiment 5

Figure 3A:
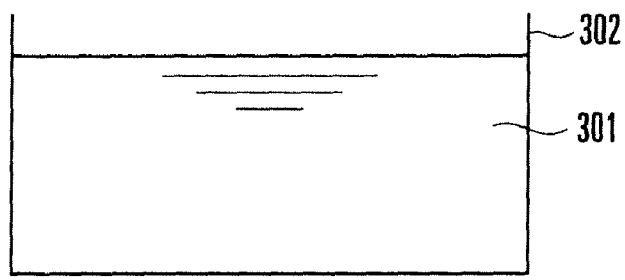
FIGS. 3A to 3E are views of steps for explaining an example of an ozone detecting device manufacturing method according to Embodiment 5 of the present invention.

Embodiment 5 of the present invention will be explained below. FIGS. 3A to 3E are views of steps for explaining an example of an ozone detecting device manufacturing method according to Embodiment 5 of the present invention. First, as shown in FIG. 3A, a vessel 302 containing a detector solution 301 is prepared. The detector solution 301 is an aqueous solution prepared by dissolving an azo dye (detector component) made of Orange I (p-(4-hydroxy-1-naphthylazo)benzenesulfonic acid, sodium salt: $C_{16}H_{11}N_2NaO_4S$) and a humectant made of glycerin ($C_3H_8O_3$), and alkalized by dissolving a base. The content of the humectant is about 20 wt %.

For example, the detector solution 301 is prepared by dissolving 0.034 g of Orange I in 25 ml of an aqueous solution in which sodium hydroxide as a base that is an alkaline substance is dissolved at a concentration of 0.1 mol/liter, and adding 10 g of glycerin and water to the solution such that the total amount is 50 g. Orange I is an azo dye (dyestuff). The detector solution 301 prepared by dissolving Orange I in an alkalized solution is a rose pink aqueous solution. The color of the detector solution 301 can be visually confirmed.

Figure 3B:

Then, as shown in FIG. 3B, a sheet-like carrier 303 having predetermined dimensions is prepared. The carrier 303 is a sheet made of fibers such as cellulose. An example is cellulose filter paper (No. 2) manufactured by ADVANTEC (TOYO FILTER PAPER). The color of the carrier 303 can be, e.g., white. Note that the carrier 303 is not limited to a sheet and may also have another shape. For example, the carrier 303 may also be a plate. As will be described later, the carrier 303 need only be a material made of fibers and capable of carrying the above-mentioned dye and alkaline substance by impregnating the material with the detector solution 301.

Figure 3C:
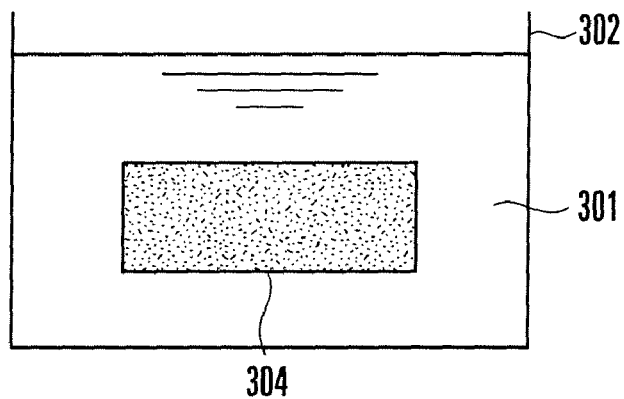

Subsequently, the prepared carrier 303 is dipped in the detector solution 301 for, e.g., 30 sec so as to impregnate the carrier 303 with the detector solution 301, thereby forming an impregnated carrier 304 impregnated with the detector solution 301 as shown in FIG. 3C. In this state, the impregnated carrier 304 is dyed by Orange I as a dyestuff.

Figure 3D:
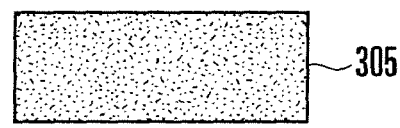
Figure 3E:
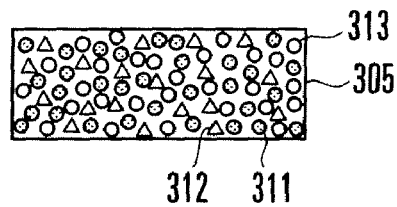

After that, the impregnated carrier 304 is pulled up from the detector solution 301, and dried in dry nitrogen by evaporating the solvent (medium) such as water contained in the impregnated carrier 304, thereby forming an ozone detecting device 305 as shown in FIG. 3D. As shown in FIG. 3E, the ozone detecting device 305 thus formed carries Orange I as an azo dye having a hydroxy group as a dye 311, together with sodium hydroxide as an alkaline substance 312. The ozone detecting device 305 also carries glycerin as a humectant 313. The obtained ozone detecting device 305 is rose pink (dyed to be rose pink), and this color can be visually confirmed. Note that "carry" mentioned above indicates the state in which substances such as a dye, alkaline substance, and humectant chemically, physically, or electrically combine with a carrier (substrate), e.g., the state in which a sheet made of fibers such as cellulose is coated and/or impregnated with a dye.

When the ozone detecting device 305 manufactured as described above is exposed to an environment in which ozone exists, the concentration of rose pink gradually decreases with the elapse of the exposure time, and the color finally changes to white. For example, the color changes to white (returns to the original color of the filter paper) when the ozone detecting device 305 is exposed to an environment in which the ozone concentration is 0.1 ppm for 5 hrs. This color change is presumably discoloration corresponding to decomposition of Orange I as an azo dye by ozone. Thus, the ozone detecting device 305 is capable of detecting ozone by the color change, and also capable of cumulative detection. The above-mentioned color change can be visually confirmed, so the ozone detecting device 305 can simply detect the cumulative amount of ozone. Also, the sheet-like carrier allows an individual to easily carry the device. As described above, the ozone detecting device of the present invention can very simply measure ozone without any large-scale apparatus, electric power, and special carrier.

A usable dye is not limited to Orange I, and it is possible to use an azo dye (dyestuff) having, in a benzene ring or naphthalene ring, a hydroxy (—OH) group bonded to the o-position or p-position of an azo group. Examples are Orange II (p-(2-hydroxy-1-naphthylazo)benzenesulfonic acid, sodium salt: $C_{16}H_{11}N_2NaO_4S$), Crocein Orange G (6-hydroxy-5-phenylazo-2-naphthalenesulfonic acid, sodium salt: $C_{16}H_{11}N_2O_4NaS$), and Tropaeoline O (4-(2,4-dihydroxyphenylazo)benzenesulfonic acid, sodium salt: $C_{12}H_9N_2NaO_5S$).

It is also possible to use an azo dye having, in both a benzene ring and naphthalene ring, two hydroxy groups adjacently bonded to an azo group. Examples are Acid Alizarin Violet N (4-hydroxy-3-(2-hydroxy-1-naphthylazo)benzenesulfonic acid, sodium salt: $C_{16}H_{11}N_2NaO_5S$) and Mordant Blue 13 (4-(5-chloro-2-hydroxyphenylazo)-3,5-dihydroxy-1,7-naphthalene disulfonic acid, disodium salt: $C_{16}H_9ClN_2Na_2O_9S_2$). These azo dyes have two hydroxy groups adjacently bonded to an azo group on different sides of the azo group.

Furthermore, it is possible to use an azo dye having, in both of two naphthalene rings, a hydroxy group adjacently bonded to an azo group. An example is calcon (2-hydroxy-1-naphthylazo)-2-naphthol 4-sulfonic acid, sodium salt: $C_2OH_{13}N_2NaO_5S$). This azo dye also has two hydroxy groups adjacently bonded to an azo group on different sides of the azo group.

The above-mentioned azo dyes each have a hydroxy group and a sulfurous acid group bonded to a position not adjacent to an azo group. As is well known, these azo dyes have a high light resistance and a high resistance against ultraviolet radiation. Even in an environment in which ultraviolet rays are radiated, therefore, these azo dyes are not largely influenced by this ultraviolet radiation, and can detect ozone with higher accuracy. The azo dye is produced by diazo coupling occurring between diazonium and an aromatic ring, and nitrous acid ions are used in the process of the production. Accordingly, the azo dye hardly reacts with $NO_x$ and the like, and can selectively detect ozone gas in environmental measurement.

Also, the ozone detecting device 305 obtained by the manufacturing method shown in FIG. 3 is formed by impregnation with the detector solution 301 containing about 20 wt % of the humectant. This more effectively achieves the color change (ozone detecting capability) caused by the existence of ozone. That is, the reaction between the dye and ozone in the ozone detecting device 305 is presumably accelerated because the humectant is contained (carried). However, if the concentration of the humectant in the detector solution is too high, e.g., exceeds 50%, the time required for drying becomes enormous. This makes it difficult to manufacture a detecting device having high reproducibility.

The relationship between the amount of humectant and the color change of the ozone detecting device caused by the existence of ozone will be explained below. That is, the comparison of a plurality of samples (ozone detecting devices) manufactured by changing the humectant amount (content) in the detector solution 301 will be explained. Note that the following explanation includes the conditions of states (acidic and neutral states) other than an alkaline state.

Figure 4:
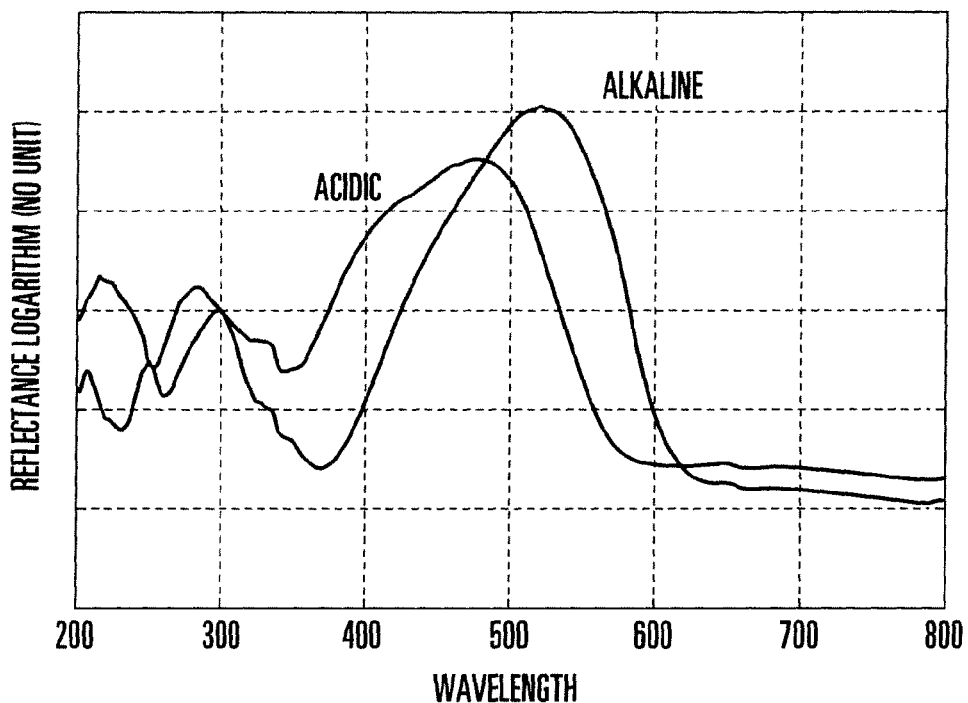
FIG. 4 is a graph showing the spectra of Orange I.

First, 0.034 g of Orange I are dissolved in 25 ml of an aqueous 0.1-mol/liter sodium hydroxide solution, and water is added to the solution such that the total amount is 50 g, thereby preparing (forming) detector solution A-3. The formed detector solution does not contain glycerin as a humectant. Ozone detecting device A-3 is formed by using detector solution A-3 in the same manner as described above. The color of ozone detecting device A-3 thus formed is rose pink. Note that Orange I has different spectral characteristics in an alkaline state and acidic state as shown in FIG. 4.

Also, 0.034 g of Orange I are dissolved in 25 ml of an aqueous 0.1-mol/liter sodium hydroxide solution, and 5 g of glycerin as a humectant and water are added to the solution to make 50 g, thereby forming detector solution B-3. Ozone detecting device B-3 is formed by using detector solution B-3 in the same manner as described above. The color of ozone detecting device B-3 thus formed is rose pink.

In addition, 0.034 g of Orange I are dissolved in 25 ml of an aqueous 0.1-mol/liter sodium hydroxide solution, and 10 g of glycerin as a humectant and water are added to the solution to make 50 g, thereby forming detector solution C-3. Ozone detecting device C-3 is formed by using detector solution C-3 in the same manner as described above. The color of ozone detecting device C-3 thus formed is rose pink.

Likewise, 0.034 g of Orange I are dissolved in 25 ml of an aqueous 0.1-mol/liter sodium hydroxide solution, and 15 g of glycerin as a humectant and water are added to the solution such that the total amount is 50 g, thereby forming detector solution D-3. Ozone detecting device D-3 is formed by using detector solution D-3 in the same manner as described above. The color of ozone detecting device D-3 thus formed is rose pink.

Also, 0.034 g of Orange I are dissolved in 25 ml of an aqueous 0.1-mol/liter sodium hydroxide solution, and 20 g of glycerin as a humectant and water are added to the solution such that the total amount is 50 g, thereby forming detector solution E-3. Ozone detecting device E-3 is formed by using detector solution E-3 in the same manner as described above. The color of ozone detecting device E-3 thus formed is rose pink.

Furthermore, detector solution F-3 is formed by adding water to 0.034 g of Orange I, 3.0 g of citric acid, and 10 g of glycerin as a humectant such that the total amount is 50 g, and ozone detecting device F-3 is formed by using detector solution F-3 in the same manner as described above. The color of ozone detecting device F-3 thus formed is orange. Ozone detecting device F-3 is a sample acidified by adding citric acid.

Additionally, detector solution G-3 is formed by adding water to 0.034 g of Orange I and 10 g of glycerin as a humectant such that the total amount is 50 g, and ozone detecting device G-3 is formed by using detector solution G-3 in the same manner as described above. The color of ozone detecting device G-3 thus formed is orange. In this sample, neither citric acid nor sodium hydroxide (a base) is added, and the pH is not adjusted by alkalization or the like.

Each of the samples (ozone detecting devices A-3, B-3, C-3, D-3, E-3, F-3, and G-3) described above was left to stand for 5 hrs in a box filled with air in which the ozone concentration was 0.1 ppm at 25° C. and a humidity of 60%, thereby conducting an ozone gas exposure test. The color change as a result of the test was checked by measuring the reflectance of the ozone detecting device at a wavelength of 525 nm. Since Orange I develops a difference color when acidified, the reflectance of ozone detecting device F-3 was measured at a wavelength of 480 nm. Note that the volume of the box is 200 liters, and, in order to analyze the internal ozone concentration, the internal air is exhausted at a rate of 2 liters/min, and air containing ozone at a predetermined concentration is supplied at a rate of 2 liters/min. Each ozone detecting device is thus exposed to the air as a detection object, and the color change of the device is measured. The color change is also visually observed. Table 8 below shows the test results.

TABLE 8

| | Orange I | | | | | | |
|---|---|---|---|---|---|---|---|
| | A-3 | B-3 | C-3 | D-3 | E-3 | F-3 | G-3 |
| Glycerin concentration (%) | 0 | 10 | 20 | 30 | 40 | 20 | 20 |
| 0.1 ppm × 5 hrs discoloration properties | 0.00 | 0.30 | 0.38 | 0.23 | 0.12 | 0.00 | 0.05 |
| Visual confirmation | Impossible | Possible | Possible | Possible | Possible | Impossible | Impossible |

The results shown in Table 8 reveal that detecting devices B-3 to E-3 containing the humectant can reliably detect ozone by cumulation of five-hour exposure even when the ozone concentration is as low as 0.1 ppm. Table 8 also shows that the amount (ratio) of humectant in the detector solution used when forming the ozone detecting device changes the color change amount per unit time of the formed detecting device. When using glycerin as the humectant, the color change amount per unit time increases as the amount of glycerin increases if the content in the detector solution is 20% or less. Furthermore, since detecting device A-3 cannot detect ozone, detection is almost impossible if no humectant is used. The results shown in Table 8 demonstrate that when using Orange I, the concentration of glycerin in the detector solution is preferably 10% to 40%, and most preferably 20%.

Also, even when using the humectant, if the detecting device is formed using an acidic detector solution as indicated by detecting device F-3, no color change is detected, so ozone detection is almost impossible. Likewise, even when using the humectant, if the detector solution is not alkalized by adjusting the pH by adding a base or acid as indicated by detecting device G-3, the detected color change is small and cannot be visually confirmed.

Embodiment 6

Figure 5:
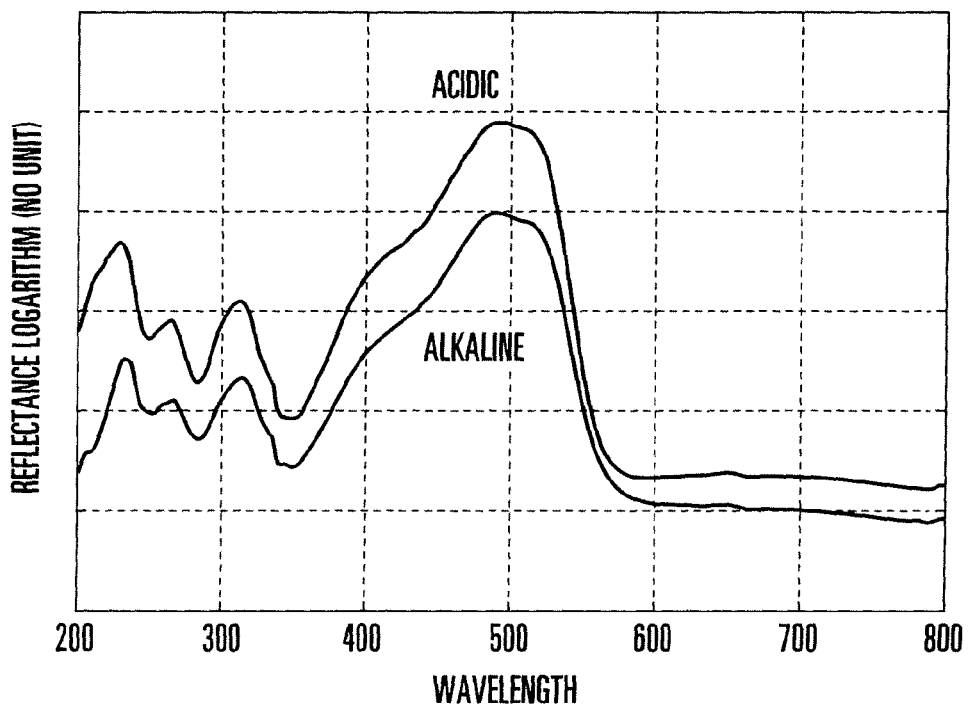
FIG. 5 is a graph showing the spectra of Orange II.

An ozone detecting device according to Embodiment 6 of the present invention will be explained below. In this embodiment, the case in which Orange II was used as an azo dye instead of Orange I described above will be explained. First, 0.034 g of Orange II are dissolved in 25 ml of an aqueous 0.1-mol/liter sodium hydroxide solution, and water is added to the solution such that the total amount is 50 g, thereby forming detector solution A-4. The formed detector solution does not contain glycerin as a humectant. Ozone detecting device A-4 is formed by using detector solution A-4 in the same manner as described above. The color of ozone detecting device A-4 thus formed is orange. Note that Orange II has slightly different spectral characteristics in an alkaline state and acidic state as shown in FIG. 5, although the peak positions are almost the same.

Also, 0.034 g of Orange II are dissolved in 25 ml of an aqueous 0.1-mol/liter sodium hydroxide solution, and 5 g of glycerin as a humectant and water are added to the solution to make 50 g, thereby forming detector solution B-4. Ozone detecting device B-4 is formed by using detector solution B-4 in the same manner as described above. The color of ozone detecting device B-4 thus formed is orange.

In addition, 0.034 g of Orange II are dissolved in 25 ml of an aqueous 0.1-mol/liter sodium hydroxide solution, and 10 g of glycerin as a humectant and water are added to the solution to make 50 g, thereby forming detector solution C-4. Ozone detecting device C-4 is formed by using detector solution C-4 in the same manner as described above. The color of ozone detecting device C-4 thus formed is orange.

Similarly, 0.034 g of Orange II are dissolved in 25 ml of an aqueous 0.1-mol/liter sodium hydroxide solution, and 15 g of glycerin as a humectant and water are added to the solution to make 50 g, thereby forming detector solution D-4. Ozone detecting device D-4 is formed by using detector solution D-4 in the same manner as described above. The color of ozone detecting device D-4 thus formed is orange.

Also, 0.034 g of Orange II are dissolved in 25 ml of an aqueous 0.1-mol/liter sodium hydroxide solution, and 20 g of glycerin as a humectant and water are added to the solution to make 50 g, thereby forming detector solution E-4. Ozone detecting device E-4 is formed by using detector solution E-4 in the same manner as described above. The color of ozone detecting device E-4 thus formed is orange.

Furthermore, detector solution F-4 is formed by adding water to 0.034 g of Orange II, 3.0 g of citric acid, and 10 g of glycerin as a humectant such that the total amount is 50 g, and ozone detecting device F-4 is formed by using detector solution F-4 in the same manner as described above. The color of ozone detecting device F-4 thus formed is orange. Ozone detecting device F-4 is a sample acidified by adding citric acid.

Additionally, detector solution G-4 is formed by adding water to 0.034 g of Orange II and 10 g of glycerin as a humectant such that the total amount is 50 g, and ozone detecting device G-4 is formed by using detector solution G-4 in the same manner as described above. The color of ozone detecting device G-4 thus formed is orange. In this sample, neither citric acid nor sodium hydroxide (a base) is added, and the pH is not adjusted by alkalization or the like.

Each of the samples (ozone detecting devices A-4, B-4, C-4, D-4, E-4, F-4, and G-4) described above was left to stand for 5 hrs in a box filled with air in which the ozone concentration was 0.1 ppm at 25° C. and a humidity of 60%, thereby conducting an ozone gas exposure test. The color change as a result of the test was checked by measuring the reflectance of the ozone detecting device at a wavelength of 500 nm. Since the maximum portion of the spectrum of Orange II includes 500 nm even in an acidic state, the reflectance of ozone detecting device F-4 was also measured at a wavelength of 500 nm. Note that the volume of the box is 200 liters, and, in order to analyze the internal ozone concentration, the internal air is exhausted at a rate of 2 liters/min, and air containing ozone at a predetermined concentration is supplied at a rate of 2 liters/min. Each ozone detecting device is thus exposed to the air as a detection object, and the color change of the device is measured. The color change is also visually observed. Table 9 below shows the test results.

TABLE 9

| | Orange II | | | | | | |
|---|---|---|---|---|---|---|---|
| | A-4 | B-4 | C-4 | D-4 | E-4 | F-4 | G-4 |
| Glycerin concentration (%) | 0 | 10 | 20 | 30 | 40 | 20 | 20 |
| 0.1 ppm × 5 hrs discoloration properties | 0.00 | 0.03 | 0.08 | 0.06 | 0.02 | 0.00 | 0.01 |
| Visual confirmation | Impossible | Impossible | Possible | Possible | Impossible | Impossible | Impossible |

The results shown in Table 9 reveal that detecting devices C-4 and D-4 containing the humectant can reliably detect ozone by cumulation of five-hour exposure even when the ozone concentration is as low as 0.1 ppm. Table 9 also shows that the amount (ratio) of humectant in the detector solution used when forming the ozone detecting device changes the color change amount per unit time of the formed detecting device. When using glycerin as the humectant, the color change amount per unit time increases as the amount of glycerin increases if the content in the detector solution is 20% or less. Furthermore, since detecting device A-4 cannot detect ozone, detection is almost impossible if no humectant is used. The results shown in Table 9 demonstrate that when using Orange II, the concentration of glycerin in the detector solution is preferably 20% to 30%, and most preferably 20%.

Also, even when using the humectant at the same concentration as that of detecting device C-4, if the detecting device is formed using an acidic detector solution as indicated by detecting device F-4, no color change is detected, so ozone detection is almost impossible. Likewise, even when using the humectant, if the detector solution is not alkalized by adjusting the pH by adding a base or acid as indicated by detecting device G-4, the detected color change is small and cannot be visually confirmed.

Embodiment 7

Figure 6:
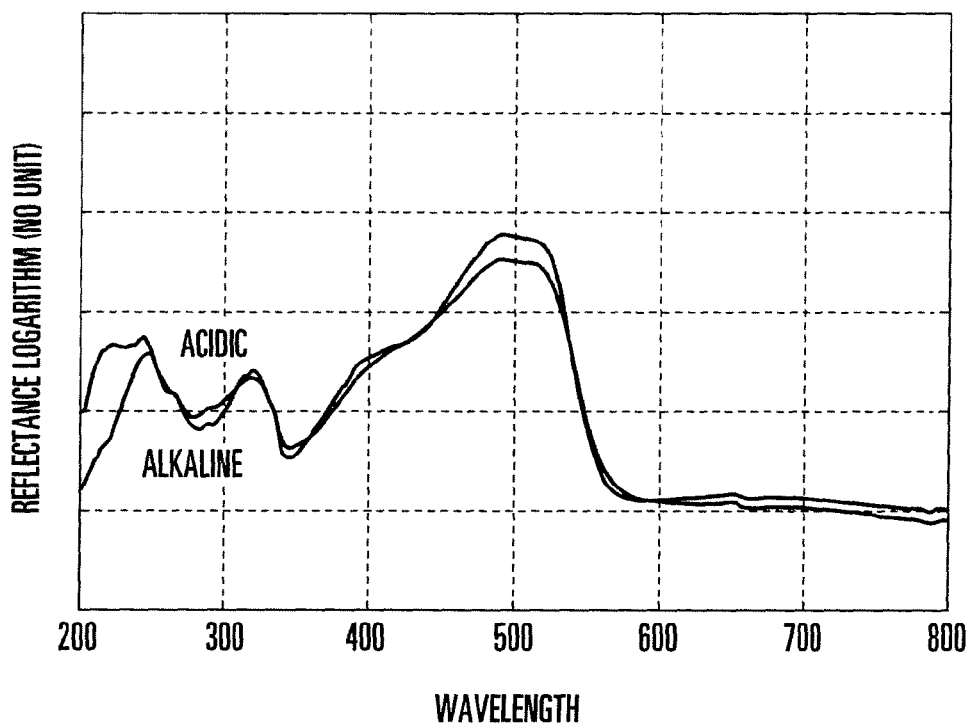
FIG. 6 is a graph showing the spectra of Crocein Orange G.

An ozone detecting device according to Embodiment 7 of the present invention will be explained below. In this embodiment, the case in which Crocein Orange G was used as an azo dye instead of Orange I and Orange II described above will be explained. First, 0.034 g of Crocein Orange G are dissolved in 25 ml of an aqueous 0.1-mol/liter sodium hydroxide solution, and water is added to the solution such that the total amount is 50 g, thereby forming detector solution A-5. The formed detector solution does not contain glycerin as a humectant. Ozone detecting device A-5 is formed by using detector solution A-5 in the same manner as described above. The color of ozone detecting device A-5 thus formed is orange. Note that Crocein Orange G has similar spectral characteristics in an alkaline state and acidic state as shown in FIG. 6.

Also, 0.034 g of Crocein Orange G are dissolved in 25 ml of an aqueous 0.1-mol/liter sodium hydroxide solution, and 5 g of glycerin as a humectant and water are added to the solution to make 50 g, thereby forming detector solution B-5. Ozone detecting device B-5 is formed by using detector solution B-5 in the same manner as described above. The color of ozone detecting device B-5 thus formed is orange.

In addition, 0.034 g of Crocein Orange G are dissolved in 25 ml of an aqueous 0.1-mol/liter sodium hydroxide solution, and 10 g of glycerin as a humectant and water are added to the solution to make 50 g, thereby forming detector solution C-5. Ozone detecting device C-5 is formed by using detector solution C-5 in the same manner as described above. The color of ozone detecting device C-5 thus formed is orange.

Analogously, 0.034 g of Crocein Orange G are dissolved in 25 ml of an aqueous 0.1-mol/liter sodium hydroxide solution, and 15 g of glycerin as a humectant and water are added to the solution to make 50 g, thereby forming detector solution D-5. Ozone detecting device D-5 is formed by using detector solution D-5 in the same manner as described above. The color of ozone detecting device D-5 thus formed is orange.

Also, 0.034 g of Crocein Orange G are dissolved in 25 ml of an aqueous 0.1-mol/liter sodium hydroxide solution, and 20 g of glycerin as a humectant and water are added to the solution to make 50 g, thereby forming detector solution E-5. Ozone detecting device E-5 is formed by using detector solution E-5 in the same manner as described above. The color of ozone detecting device E-5 thus formed is orange.

Furthermore, detector solution F-5 is formed by adding water to 0.034 g of Crocein Orange G, 3.0 g of citric acid, and 10 g of glycerin as a humectant such that the total amount is 50 g, and ozone detecting device F-5 is formed by using detector solution F-5 in the same manner as described above. The color of ozone detecting device F-5 thus formed is orange. Ozone detecting device F-5 is a sample acidified by adding citric acid.

Additionally, detector solution G-5 is formed by adding water to 0.034 g of Crocein Orange G and 10 g of glycerin as a humectant such that the total amount is 50 g, and ozone detecting device G-5 is formed by using detector solution G-5 in the same manner as described above. The color of ozone detecting device G-5 thus formed is orange. In this sample, neither citric acid nor sodium hydroxide (a base) is added, and the pH is not adjusted by alkalization or the like.

Each of the samples (ozone detecting devices A-5, B-5, C-5, D-5, E-5, F-5, and G-5) described above was left to stand for 5 hrs in a box filled with air in which the ozone concentration was 0.1 ppm at 25° C. and a humidity of 60%, thereby conducting an ozone gas exposure test. The color change as a result of the test was checked by measuring the reflectance of the ozone detecting device at a wavelength of 500 nm. Since the maximum portion of the spectrum of Crocein Orange O includes 500 nm even in the acidic state, the reflectance of ozone detecting device F-5 was also measured at a wavelength of 500 nm. Note that the volume of the box is 200 liters, and, in order to analyze the internal ozone concentration, the internal air is exhausted at a rate of 2 liters/min, and air containing ozone at a predetermined concentration is supplied at a rate of 2 liters/min. Each ozone detecting device is thus exposed to the air as a detection object, and the color change of the device is measured. The color change is also visually observed. Table 10 below shows the test results.

TABLE 10

| | Crocein Orange G | | | | | | |
|---|---|---|---|---|---|---|---|
| | A-5 | B-5 | C-5 | D-5 | E-5 | F-5 | G-5 |
| Glycerin concentration (%) | 0 | 10 | 20 | 30 | 40 | 20 | 20 |
| 0.1 ppm × 5 hrs discoloration properties | 0.00 | 0.10 | 0.15 | 0.08 | 0.03 | 0.00 | 0.01 |
| Visual confirmation | Impossible | Possible | Possible | Possible | Impossible | Impossible | Impossible |

The results shown in Table 10 reveal that detecting devices B-5, C-5, and D-5 containing the humectant can reliably detect ozone by cumulation of five-hour exposure even when the ozone concentration is as low as 0.1 ppm. Table 10 also shows that the amount (ratio) of humectant in the detector solution used when forming the ozone detecting device changes the color change amount per unit time of the formed detecting device. When using glycerin as the humectant, the color change amount per unit time increases as the amount of glycerin increases if the content in the detector solution is 20% or less. Furthermore, since detecting device A-5 cannot detect ozone, detection is almost impossible if no humectant is used. The results shown in Table 10 demonstrate that when using Crocein Orange G, the concentration of glycerin in the detector solution is preferably 10% to 30%, and most preferably 20%.

Also, even when using the humectant at the same concentration as that of detecting device C-5, if the detecting device is formed using an acidic detector solution as indicated by detecting device F-5, no color change is detected, so ozone detection is almost impossible. Likewise, even when using the humectant, if the detector solution is not alkalized by adjusting the pH by adding a base or acid as indicated by detecting device G-5, the detected color change is small and cannot be visually confirmed.

Embodiment 8

Figure 7:
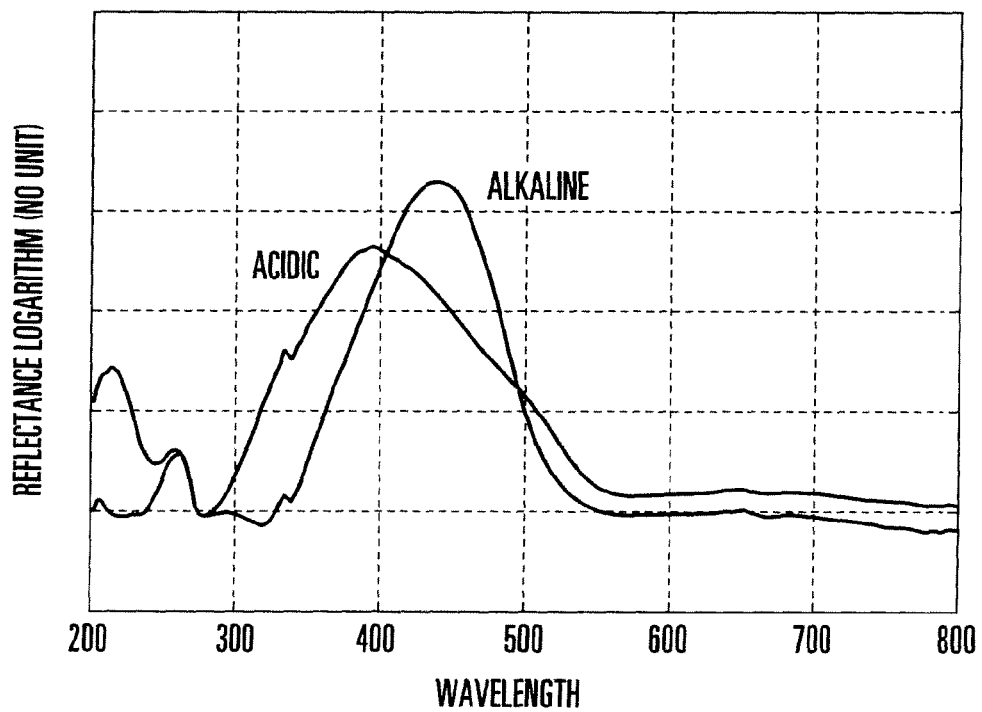
FIG. 7 is a graph showing the spectra of Tropaeoline O.

An ozone detecting device according to Embodiment 8 of the present invention will be explained below. In this embodiment, the case in which Tropaeoline O was used as an azo dye will be explained. First, 0.03 g of Tropaeolin O are dissolved in 25 ml of an aqueous 0.1-mol/liter sodium hydroxide solution, and water is added to the solution such that the total amount is 50 g, thereby forming detector solution A-6. The formed detector solution does not contain glycerin as a humectant. Ozone detecting device A-6 is formed by using detector solution A-6 in the same manner as described above. The color of ozone detecting device A-6 thus formed is yellow. Note that Tropaeolin O has slightly different spectral characteristics in an alkaline state and acidic state as shown in FIG. 7.

Also, 0.03 g of Tropaeolin O are dissolved in 25 ml of an aqueous 0.1-mol/liter sodium hydroxide solution, and 5 g of glycerin as a humectant and water are added to the solution to make 50 g, thereby forming detector solution B-6. Ozone detecting device B-6 is formed by using detector solution B-6 in the same manner as described above. The color of ozone detecting device B-6 thus formed is yellow.

In addition, 0.03 g of Tropaeolin O are dissolved in 25 ml of an aqueous 0.1-mol/liter sodium hydroxide solution, and 10 g of glycerin as a humectant and water are added to the solution to make 50 g, thereby forming detector solution C-6. Ozone detecting device C-6 is formed by using detector solution C-6 in the same manner as described above. The color of ozone detecting device C-6 thus formed is yellow.

Analogously, 0.03 g of Tropaeolin O are dissolved in 25 ml of an aqueous 0.1-mol/liter sodium hydroxide solution, and 15 g of glycerin as a humectant and water are added to the solution to make 50 g, thereby forming detector solution D-6. Ozone detecting device D-6 is formed by using detector solution D-6 in the same manner as described above. The color of ozone detecting device D-6 thus formed is yellow.

Also, 0.03 g of Tropaeolin O are dissolved in 25 ml of an aqueous 0.1-mol/liter sodium hydroxide solution, and 20 g of glycerin as a humectant and water are added to the solution to make 50 g, thereby forming detector solution E-6. Ozone detecting device E-6 is formed by using detector solution E-6 in the same manner as described above. The color of ozone detecting device E-6 thus formed is yellow.

Furthermore, detector solution F-6 is formed by adding water to 0.03 g of Tropaeolin O, 3.0 g of citric acid, and 10 g of glycerin as a humectant such that the total amount is 50 g, and ozone detecting device F-6 is formed by using detector solution F-6 in the same manner as described above. The color of ozone detecting device F-6 thus formed is yellow. Ozone detecting device F-6 is a sample acidified by adding citric acid.

Additionally, detector solution G-6 is formed by adding water to 0.03 g of Tropaeolin O and 10 g of glycerin as a humectant such that the total amount is 50 g, and ozone detecting device G-6 is formed by using detector solution G-6 in the same manner as described above. The color of ozone detecting device G-6 thus formed is yellow. In this sample, neither citric acid nor sodium hydroxide (a base) is added, and the pH is not adjusted by alkalization or the like.

Each of the samples (ozone detecting devices A-6, B-6, C-6, D-6, E-6, F-6, and G-6) described above was left to stand for 5 hrs in a box filled with air in which the ozone concentration was 0.1 ppm at 25° C. and a humidity of 60%, thereby conducting an ozone gas exposure test. The color change as a result of the test was checked by measuring the reflectance of the ozone detecting device at a wavelength of 440 nm. Since Tropaeolin O develops a different color when acidified, the reflectance of ozone detecting device F-6 was measured at a wavelength of 400 nm. Note that the volume of the box is 200 liters, and, in order to analyze the internal ozone concentration, the internal air is exhausted at a rate of 2 liters/min, and air containing ozone at a predetermined concentration is supplied at a rate of 2 liters/min. Each ozone detecting device is thus exposed to the air as a detection object, and the color change of the device is measured. The color change is also visually observed. Table 11 below shows the test results.

TABLE 11

| | Tropaeolin O | | | | | | |
|---|---|---|---|---|---|---|---|
| | A-6 | B-6 | C-6 | D-6 | E-6 | F-6 | G-6 |
| Glycerin concentration (%) | 0 | 10 | 20 | 30 | 40 | 20 | 20 |
| 0.1 ppm × 5 hrs discoloration properties | 0.00 | 0.06 | 0.26 | 0.32 | 0.16 | 0.00 | 0.03 |
| Visual confirmation | Impossible | Impossible | Possible | Possible | Possible | Impossible | Impossible |

The results shown in Table 11 reveal that detecting devices C-6, D-6, and E-6 containing the humectant can reliably detect ozone by cumulation of five-hour exposure even when the ozone concentration is as low as 0.1 ppm. Table 11 also shows that the amount (ratio) of humectant in the detector solution used when forming the ozone detecting device changes the color change amount per unit time of the formed detecting device. When using glycerin as the humectant, the color change amount per unit time increases as the amount of glycerin increases if the content in the detector solution is 30% or less. Furthermore, since detecting device A-6 cannot detect ozone, detection is almost impossible if no humectant is used. The results shown in Table 11 demonstrate that when using Tropaeolin O, the concentration of glycerin in the detector solution is preferably 20% to 40%, and most preferably 30%.

Also, even when using the humectant at the same concentration as that of detecting device C-6, if the detecting device is formed using an acidic detector solution as indicated by detecting device F-6, no color change is detected, so ozone detection is almost impossible. Likewise, even when using the humectant, if the detector solution is not alkalized by adjusting the pH by adding a base or acid as indicated by detecting device G-6, the detected color change is small and cannot be visually confirmed.

Note that Orange I, Orange II, Crocein Orange G, and Tropaeolin O described above each have one hydroxy group and no sulfurous acid group ($SO_3$ group) adjacent to an azo group, in a benzene ring or naphthalene ring. In other words, the above dye is an azo dye which has one hydroxy group, and in which the $SO_3$ group is bonded to a position except for the o-position of the azo group. Note that the hydroxy group is bonded to the o-position or p-position of the azo group.

Embodiment 9

Figure 8:
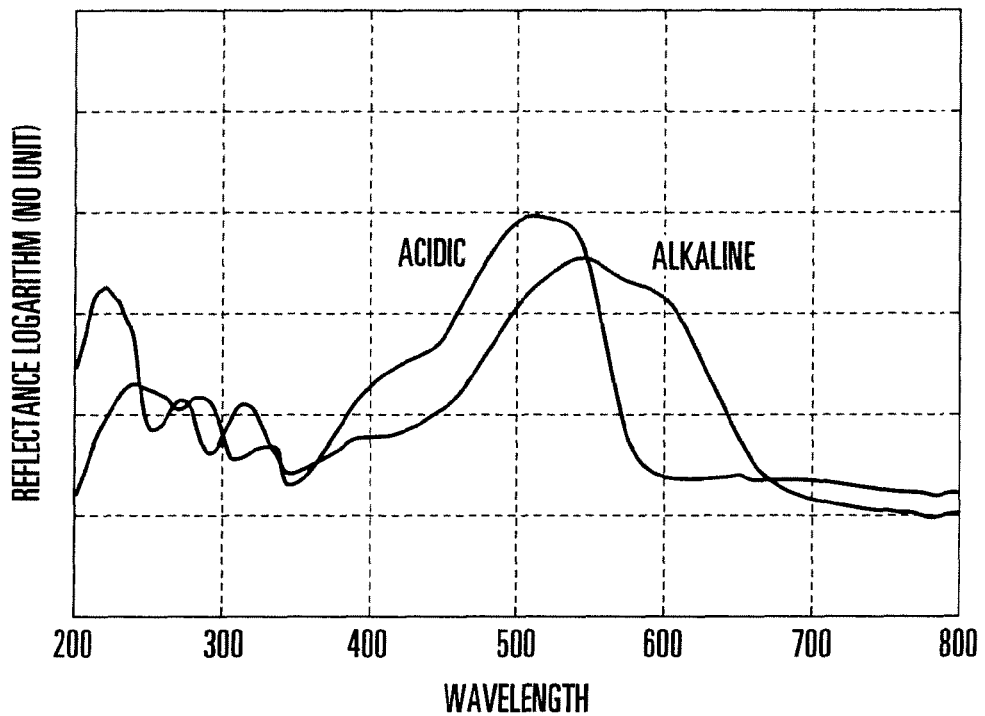
FIG. 8 is a graph showing the spectra of Acid Alizarin Violet N.

An ozone detecting device according to Embodiment 9 of the present invention will be explained below. In this embodiment, the case in which Acid Alizarin Violet N was used as an azo dye will be explained. First, 0.035 g of Acid Alizarin Violet N are dissolved in 25 ml of an aqueous 0.1-mol/liter sodium hydroxide solution, and water is added to the solution such that the total amount is 50 g, thereby forming detector solution A-7. The formed detector solution does not contain glycerin as a humectant. Ozone detecting device A-7 is formed by using detector solution A-7 in the same manner as described above. The color of ozone detecting device A-7 thus formed is purple. Note that Acid Alizarin Violet N has different spectral characteristics in an alkaline state (pH=9 or more) and acidic state as shown in FIG. 8.

Also, 0.035 g of Acid Alizarin Violet N are dissolved in 25 ml of an aqueous 0.1-mol/liter sodium hydroxide solution, and 5 g of glycerin as a humectant and water are added to the solution to make 50 g, thereby forming detector solution B-7. Ozone detecting device B-7 is formed by using detector solution B-7 in the same manner as described above. The color of ozone detecting device B-7 thus formed is purple.

In addition, 0.035 g of Acid Alizarin Violet N are dissolved in 25 ml of an aqueous 0.1-mol/liter sodium hydroxide solution, and 10 g of glycerin as a humectant and water are added to the solution to make 50 g, thereby forming detector solution C-7. Ozone detecting device C-7 is formed by using detector solution C-7 in the same manner as described above. The color of ozone detecting device C-7 thus formed is purple.

Analogously, 0.035 g of Acid Alizarin Violet N are dissolved in 25 ml of an aqueous 0.1-mol/liter sodium hydroxide solution, and 15 g of glycerin as a humectant and water are added to the solution to make 50 g, thereby forming detector solution D-7. Ozone detecting device D-7 is formed by using detector solution D-7 in the same manner as described above. The color of ozone detecting device D-7 thus formed is purple.

Also, 0.035 g of Acid Alizarin Violet N are dissolved in 25 ml of an aqueous 0.1-mol/liter sodium hydroxide solution, and 20 g of glycerin as a humectant and water are added to the solution to make 50 g, thereby forming detector solution E-7. Ozone detecting device E-7 is formed by using detector solution E-7 in the same manner as described above. The color of ozone detecting device E-7 thus formed is purple.

Furthermore, detector solution F-7 is formed by adding water to 0.035 g of Acid Alizarin Violet N, 3.0 g of citric acid, and 10 g of glycerin as a humectant such that the total amount is 50 g, and ozone detecting device F-7 is formed by using detector solution F-7 in the same manner as described above. The color of ozone detecting device F-7 thus formed is orange. Ozone detecting device F-7 is a sample acidified by adding citric acid.

Additionally, detector solution G-7 is formed by adding water to 0.035 g of Acid Alizarin Violet N and 10 g of glycerin as a humectant such that the total amount is 50 g, and ozone detecting device G-7 is formed by using detector solution G-7 in the same manner as described above. The color of ozone detecting device G-7 thus formed is purple. In this sample, neither citric acid nor sodium hydroxide (a base) is added, and the pH is not adjusted by alkalization or the like.

Each of the samples (ozone detecting devices A-7, B-7, C-7, D-7, E-7, F-7, and G-7) described above was left to stand for 5 hrs in a box filled with air in which the ozone concentration was 0.1 ppm at 25° C. and a humidity of 60%, thereby conducting an ozone gas exposure test. The color change as a result of the test was checked by measuring the reflectance of the ozone detecting device at a wavelength of 530 nm. Since Acid Alizarin Violet N develops a different color when acidified, the reflectance of ozone detecting device F-7 was measured at a wavelength of 510 nm. Note that the volume of the box is 200 liters, and, in order to analyze the internal ozone concentration, the internal air is exhausted at a rate of 2 liters/min, and air containing ozone at a predetermined concentration is supplied at a rate of 2 liters/min. Each ozone detecting device is thus exposed to the air as a detection object, and the color change of the device is measured. The color change is also visually observed. Table 12 below shows the test results.

TABLE 12

| Acid Alizarin Violet N | | | | | | | |
|---|---|---|---|---|---|---|---|
| | A-7 | B-7 | C-7 | D-7 | E-7 | F-7 | G-7 |
| Glycerin concentration (%) | 0 | 10 | 20 | 30 | 40 | 20 | 20 |

TABLE 12-continued

| Acid Alizarin Violet N | | | | | | | |
|---|---|---|---|---|---|---|---|
| | A-7 | B-7 | C-7 | D-7 | E-7 | F-7 | G-7 |
| 0.1 ppm × 5 hrs discoloration properties | 0.01 | 0.16 | 0.17 | 0.11 | 0.05 | 0.00 | 0.18 |
| Visual confirmation | Impossible | Possible | Possible | Possible | Impossible | Impossible | Possible |

The results shown in Table 12 reveal that detecting devices B-7, C-7, and D-7 containing the humectant can reliably detect ozone by cumulation of five-hour exposure even when the ozone concentration is as low as 0.1 ppm. Table 12 also shows that the amount (ratio) of humectant in the detector solution used when forming the ozone detecting device changes the color change amount per unit time of the formed detecting device. When using glycerin as the humectant, the color change amount per unit time increases as the amount of glycerin increases if the content in the detector solution is 20% or less. Furthermore, since detecting device A-7 cannot detect ozone, detection is almost impossible if no humectant is used. The results shown in Table 12 demonstrate that when using Acid Alizarin Violet N, the concentration of glycerin in the detector solution is preferably 10% to 30%, and most preferably 20%.

Also, even when using the humectant at the same concentration as that of detecting device C-7, if the detecting device is formed using an acidic detector solution as indicated by detecting device F-7, no color change is detected, so ozone detection is almost impossible. By contrast, as indicated by detecting device G-7, even when no alkalization is performed, if the pH is not adjusted by adding a base or acid, ozone can be detected in the same way as when using detecting device C-7, provided that the humectant is used. This state can also be expressed as an unacidified state.

Embodiment 10

Figure 9:
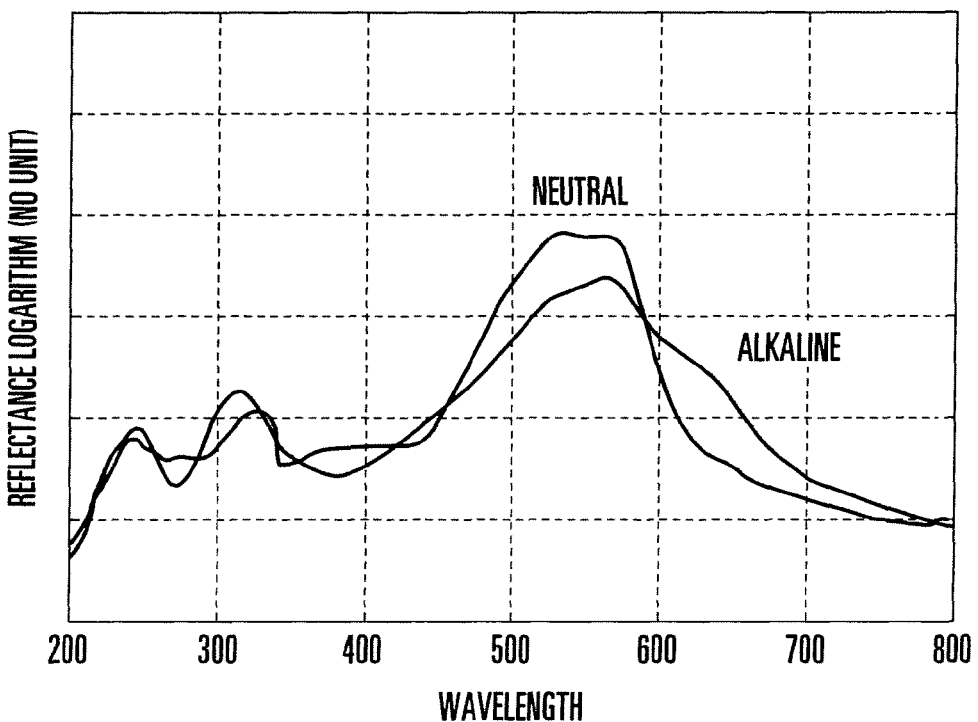
FIG. 9 is a graph showing the spectra of Mordant Blue 13.

An ozone detecting device according to Embodiment 10 of the present invention will be explained below. In this embodiment, the case in which Mordant Blue 13 was used as an azo dye instead of Acid Alizarin Violet N will be explained. First, 0.053 g of Mordant Blue 13 are dissolved in 25 ml of an aqueous 0.1-mol/liter sodium hydroxide solution, and water is added to the solution such that the total amount is 50 g, thereby forming detector solution A-8. The formed detector solution does not contain glycerin as a humectant. Ozone detecting device A-8 is formed by using detector solution A-8 in the same manner as described above. The color of ozone detecting device A-8 thus formed is lavender. Note that Mordant Blue 13 has different spectral characteristics in an alkaline state and acidic state as shown in FIG. 9.

Also, 0.053 g of Mordant Blue 13 are dissolved in 25 ml of an aqueous 0.1-mol/liter sodium hydroxide solution, and 5 g of glycerin as a humectant and water are added to the solution to make 50 g, thereby forming detector solution B-8. Ozone detecting device B-8 is formed by using detector solution B-8 in the same manner as described above. The color of ozone detecting device B-8 thus formed is lavender.

In addition, 0.053 g of Mordant Blue 13 are dissolved in 25 ml of an aqueous 0.1-mol/liter sodium hydroxide solution, and 10 g of glycerin as a humectant and water are added to the solution to make 50 g, thereby forming detector solution C-8. Ozone detecting device C-8 is formed by using detector solution C-8 in the same manner as described above. The color of ozone detecting device C-8 thus formed is lavender.

Analogously, 0.053 g of Mordant Blue 13 are dissolved in 25 ml of an aqueous 0.1-mol/liter sodium hydroxide solution, and 15 g of glycerin as a humectant and water are added to the solution to make 50 g, thereby forming detector solution D-8. Ozone detecting device D-8 is formed by using detector solution D-8 in the same manner as described above. The color of ozone detecting device D-8 thus formed is lavender.

Also, 0.053 g of Mordant Blue 13 are dissolved in 25 ml of an aqueous 0.1-mol/liter sodium hydroxide solution, and 20 g of glycerin as a humectant and water are added to the solution to make 50 g, thereby forming detector solution E-8. Ozone detecting device E-8 is formed by using detector solution E-8 in the same manner as described above. The color of ozone detecting device E-8 thus formed is lavender.

Furthermore, detector solution F-8 is formed by adding water to 0.053 g of Mordant Blue 13, 3.0 g of citric acid, and 10 g of glycerin as a humectant such that the total amount is 50 g, and ozone detecting device F-8 is formed by using detector solution F-8 in the same manner as described above. The color of ozone detecting device F-8 thus formed is purplish red. Ozone detecting device F-8 is a sample acidified by adding citric acid.

Additionally, detector solution G-8 is formed by adding water to 0.053 g of Mordant Blue 13 and 10 g of glycerin as a humectant such that the total amount is 50 g, and ozone detecting device G-8 is formed by using detector solution G-8 in the same manner as described above. The color of ozone detecting device G-8 thus formed is lavender. In this sample, neither citric acid nor sodium hydroxide (a base) is added, and the pH is not adjusted by alkalization or the like.

Each of the samples (ozone detecting devices A-8, B-8, C-8, D-8, E-8, F-8, and G-8) described above was left to stand for 5 hrs in a box filled with air in which the ozone concentration was 0.1 ppm at 25° C. and a humidity of 60%, thereby conducting an ozone gas exposure test. The color change as a result of the test was checked by measuring the reflectance of the ozone detecting device at a wavelength of 550 nm. Since Mordant Blue 13 develops a different color when acidified, the reflectance of ozone detecting device F-8 was measured at a wavelength of 530 nm. Note that the volume of the box is 200 liters, and, in order to analyze the internal ozone concentration, the internal air is exhausted at a rate of 2 liters/min, and air containing ozone at a predetermined concentration is supplied at a rate of 2 liters/min. Each ozone detecting device is thus exposed to the air as a detection object, and the color change of the device is measured. The color change is also visually observed. Table 13 below shows the test results.

TABLE 13

| | Mordant Blue 13 | | | | | | |
|---|---|---|---|---|---|---|---|
| | A-8 | B-8 | C-8 | D-8 | E-8 | F-8 | G-8 |
| Glycerin concentration (%) | 0 | 10 | 20 | 30 | 40 | 20 | 20 |
| 0.1 ppm × 5 hrs discoloration properties | 0.01 | 0.06 | 0.07 | 0.03 | 0.02 | 0.01 | 0.07 |
| Visual confirmation | Impossible | Possible | Possible | Impossible | Impossible | Impossible | Possible |

The results shown in Table 13 reveal that detecting devices B-8 and C-8 containing the humectant can reliably detect ozone by cumulation of five-hour exposure even when the ozone concentration is as low as 0.1 ppm. Table 13 also shows that the amount (ratio) of humectant in the detector solution used when forming the ozone detecting device changes the color change amount per unit time of the formed detecting device. When using glycerin as the humectant, the color change amount per unit time increases as the amount of glycerin increases if the content in the detector solution is 20% or less. Furthermore, since detecting device A-8 cannot detect ozone, detection is almost impossible if no humectant is used. The results shown in Table 13 demonstrate that when using Mordant Blue 13, the concentration of glycerin in the detector solution is preferably 10% to 20%, and most preferably 20%.

Also, even when using the humectant at the same concentration as that of detecting device C-8, if the detecting device is formed using an acidic detector solution as indicated by detecting device F-8, no color change is detected, so ozone detection is almost impossible. By contrast, as indicated by detecting device G-8, even when no alkalization is performed, if the pH is not adjusted by adding a base or acid, ozone can be detected in the same way as when using detecting device C-8, provided that the humectant is used. This state can also be expressed as an unacidified state.

Note that Acid Alizarin Violet N and Mordant Blue 13 described above each have two hydroxy groups adjacent to an azo group and no $SO_3$ group adjacent to the azo group, in a benzene ring or naphthalene ring. In other words, the above dye is an azo dye which has two hydroxy groups in the o-position of the azo group, and in which the $SO_3$ group is bonded to a position except for the o-position of the azo group.

Embodiment 11

Figure 10:
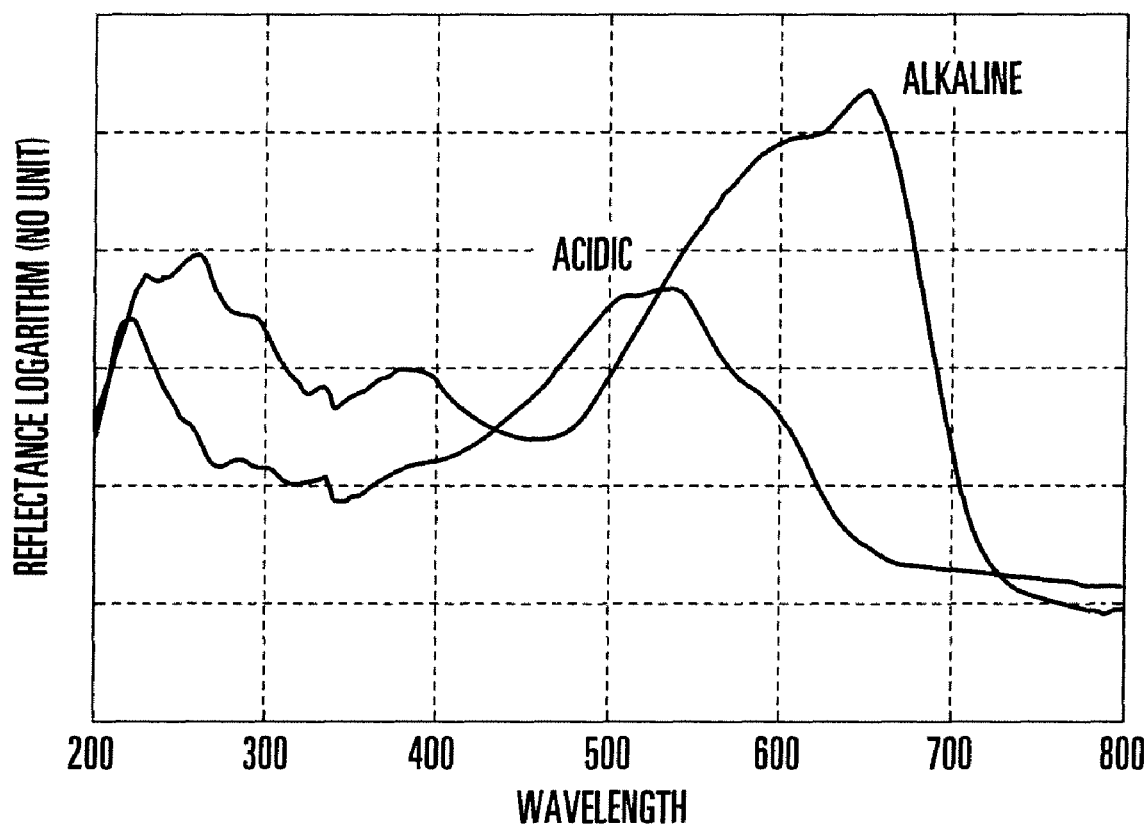
FIG. 10 is a graph showing the spectra of calcon.

An ozone detecting device according to Embodiment 11 of the present invention will be explained below. In this embodiment, the case in which calcon was used as an azo dye will be explained. First, 0.08 g of calcon are dissolved in 25 ml of an aqueous 0.1-mol/liter sodium hydroxide solution, and water is added to the solution such that the total amount is 50 g, thereby forming detector solution A-9. Calcon is an azo dye (azo dyestuff) also called Alizarin Blue Black R, and detector solution A-9 is a navy blue aqueous solution. The color of detector solution A-9 can be visually confirmed. The formed detector solution does not contain glycerin as a humectant. Ozone detecting device A-9 is formed by using detector solution A-9 in the same manner as described above. The color of ozone detecting device A-9 thus formed is navy blue. Note that calcon has different spectral characteristics in an alkaline state and acidic state as shown in FIG. 10.

Also, 0.08 g of calcon are dissolved in 25 ml of an aqueous 0.1-mol/liter sodium hydroxide solution, and 5 g of glycerin as a humectant and water are added to the solution to make 50 g, thereby forming detector solution B-9. Ozone detecting device B-9 is formed by using detector solution B-9 in the same manner as described above. The color of ozone detecting device B-9 thus formed is navy blue.

In addition, 0.08 g of calcon are dissolved in 25 ml of an aqueous 0.1-mol/liter sodium hydroxide solution, and 10 g of glycerin as a humectant and water are added to the solution to make 50 g, thereby forming detector solution C-9. Ozone detecting device C-9 is formed by using detector solution C-9 in the same manner as described above. The color of ozone detecting device C-9 thus formed is navy blue.

Analogously, 0.08 g of calcon are dissolved in 25 ml of an aqueous 0.1-mol/liter sodium hydroxide solution, and 15 g of glycerin as a humectant and water are added to the solution to make 50 g, thereby forming detector solution D-9. Ozone detecting device D-9 is formed by using detector solution D-9 in the same manner as described above. The color of ozone detecting device D-9 thus formed is navy blue.

Also, 0.08 g of calcon are dissolved in 25 ml of an aqueous 0.1-mol/liter sodium hydroxide solution, and 20 g of glycerin as a humectant and water are added to the solution to make 50 g, thereby forming detector solution E-9. Ozone detecting device E-9 is formed by using detector solution E-9 in the same manner as described above. The color of ozone detecting device E-9 thus formed is navy blue.

Furthermore, detector solution F-9 is formed by dissolving 0.08 g of calcon in 25 ml of ethanol, and adding 3.0 g of citric acid, 10 g of glycerin, and water to the solution such that the total amount is 50 g. Calcon is soluble in alkaline water but almost insoluble in neutral or acidic water. However, ethanol can increase the amount of calcon to be dissolved in neutral or acidic water. Note that many azo dyes having two naphthalene rings, such as calcon, do not exhibit high water-solubility when they are acidic or neutral, and show water-solubility when alkalized. Ozone detecting device F-9 is formed by using detector solution F-9 in the same manner as described above. The color of ozone detecting device F-9 thus formed is lavender. Ozone detecting device F-9 is a sample acidified by adding citric acid.

Additionally, detector solution G-9 is formed by dissolving 0.08 g of calcon in 25 ml of ethanol, and adding 10 g of glycerin and water to the solution such that the total amount is 50 g. Ozone detecting device G-9 is formed by using detector solution G-9 in the same manner as described above. The color of ozone detecting device G-9 thus formed is navy blue (purple). In this sample, neither citric acid nor sodium hydroxide (a base) is added, and the pH is not adjusted by alkalization or the like.

Each of the samples (ozone detecting devices A-9, B-9, C-9, D-9, E-9, F-9, and G-9) described above was left to stand for 5 hrs in a box filled with air in which the ozone concentration was 0.1 ppm at 25° C. and a humidity of 60%, thereby conducting an ozone gas exposure test. The color change as a result of the test was checked by measuring the reflectance of the ozone detecting device at a wavelength of 650 nm. Since calcon develops a different color when acidified, the reflectance of ozone detecting device F-9 was measured at a wavelength of 520 nm. Note that the volume of the box is 200 liters; and, in order to analyze the internal ozone concentration, the internal air is exhausted at a rate of 2 liters/min, and air containing ozone at a predetermined concentration is supplied at a rate of 2 liters/min. Each ozone detecting device is thus exposed to the air as a detection object, and the color change of the device is measured. The color change is also visually observed. Table 14 below shows the test results.

TABLE 14

| Calcon | | | | | | | |
|---|---|---|---|---|---|---|---|
| | A-9 | B-9 | C-9 | D-9 | E-9 | F-9 | G-9 |
| Glycerin concentration (%) | 0 | 10 | 20 | 30 | 40 | 20 | 20 |
| 0.1 ppm × 5 hrs discoloration properties | 0.01 | 0.24 | 0.35 | 0.18 | 0.06 | 0.00 | 0.35 |
| Visual confirmation | Impossible | Possible | Possible | Possible | Possible | Impossible | Possible |

The results shown in Table 14 reveal that detecting devices B-9 to E-9 containing the humectant can reliably detect ozone by cumulation of five-hour exposure even when the ozone concentration is as low as 0.1 ppm. Table 14 also shows that the amount (ratio) of humectant in the detector solution used when forming the ozone detecting device changes the color change amount per unit time of the formed detecting device. When using glycerin as the humectant, the color change amount per unit time increases as the amount of glycerin increases if the content in the detector solution is 20% or less. Furthermore, since detecting device A-9 cannot detect ozone, detection is almost impossible if no humectant is used. The results shown in Table 14 demonstrate that when using calcon, the concentration of glycerin in the detector solution is preferably 10% to 40%, and most preferably 20%.

Also, even when using the humectant at the same concentration as that of detecting device C-9, if the detecting device is formed using an acidic detector solution as indicated by detecting device F-9, no color change is detected, so ozone detection is almost impossible. By contrast, as indicated by detecting device G-9, even when no alkalization is performed, if the pH is not adjusted without adding a base or acid, ozone can be detected in the same manner as when using detecting device C-9, provided that the humectant is used. This state can also be expressed as an unacidified state.

Calcon described above is an azo dye having two hydroxy groups adjacent to an azo group on different sides of the azo group, and having no $SO_3$ group adjacent to the azo group.

Note that glycerin is used as a humectant in the embodiments described above, but the present invention is not limited to this and it is also possible to use, e.g., ethyleneglycol or propyleneglycol as will be described below. Note also that another humectant in which the above-mentioned dyes dissolve may also be used.

Comparative examples will be explained below.

In the following comparative examples, detecting devices formed in the same manner as described above by using azo dyes cannot detect ozone.

Comparative Example 4

An ozone detecting device of Comparative Example 4 will be explained below. In the following comparative example, the case in which Orange G (7-hydroxy-8-(phenylazo)-1,3-naphthalenedisulfonic acid, disodium salt: $C_{20}H_{11}N_2Na_3O_{10}S_3$) was used as an azo dye will be explained. First, 0.044 g of Orange G are dissolved in 25 ml of an aqueous 0.1-mol/liter sodium hydroxide solution, and water is added to the solution such that the total amount is 50 g, thereby forming detector solution H-3. Detector solution H-3 is an orange aqueous solution. The color of detector solution H-3 can be visually confirmed. The formed detector solution does not contain glycerin as a humectant. Ozone detecting device H-3 is formed in the same manner as described above by using detector solution H-3. The color of ozone detecting device H-3 thus formed is orange.

Also, 0.044 g of Orange G are dissolved in 25 ml of an aqueous 0.1-mol/liter sodium hydroxide solution, and 10 g of glycerin as a humectant and water are added to the solution to make 50 g, thereby forming detector solution I-3. Ozone detecting device I-3 is formed by using detector solution I-3 in the same manner as described above. The color of ozone detecting device I-3 thus formed is orange.

Furthermore, detector solution J-3 is formed by adding water to 0.044 g of Orange G, 3.0 g of citric acid, and 10 g of glycerin as a humectant such that the total amount is 50 g, and ozone detecting device J-3 is formed by using detector solution J-3 in the same manner as described above. The color of ozone detecting device J-3 thus formed is orange. Ozone detecting device J-3 is a sample acidified by adding citric acid.

Each of the samples (ozone detecting devices H-3, I-3, and J-3) described above was left to stand for 5 hrs in a box filled with air in which the ozone concentration was 0.1 ppm at 25° C. and a humidity of 60%, thereby conducting an ozone gas exposure test. The color change as a result of the test was checked by measuring the reflectance of the ozone detecting device at a wavelength of 500 nm. Since the maximum portion of the spectrum of Orange G includes 500 nm even in an acidic state, the reflectance of ozone detecting device J-3 was also measured at a wavelength of 500 nm. Note that the volume of the box is 200 liters, and, in order to analyze the internal ozone concentration, the internal air is exhausted at a rate of 2 liters/min, and air containing ozone at a predetermined concentration is supplied at a rate of 2 liters/min. Each ozone detecting device is thus exposed to the air as a detection object, and the color change of the device is measured. The color change is also visually observed. Table 15 below shows the test results.

TABLE 15

| | Orange G | | |
|---|---|---|---|
| | H-3 | I-3 | J-3 |
| Glycerin concentration (%) | 0 | 20 | 20 |
| 0.1 ppm × 5 hrs discoloration properties | 0.00 | 0.02 | 0.00 |
| Visual confirmation | Impossible | Impossible | Impossible |

The results shown in Table 15 reveal that no discoloration by ozone was found in any detecting device. When using Orange G, therefore, no ozone can be detected not only in an acidic state but also in an alkaline state. Orange G is an azo dye having an $SO_3$ group adjacently bonded to an azo group.

Comparative Example 5

An ozone detecting device of Comparative Example 5 will be explained below. In the following comparative example, the case in which New Coccine (7-hydroxy-8-(4-sulfonato-1-naphthylazo)-1,3-naphthalenedisulfonic acid, trisodium salt: $C_{20}H_{11}N_2Na_3O_{10}S_3$) was used as an azo dye will be explained. First, 0.058 g of New Coccine are dissolved in 25 ml of an aqueous 0.1-mol/liter sodium hydroxide solution, and water is added to the solution such that the total amount is 50 g, thereby forming detector solution H-4. Detector solution H-4 is a rose pink aqueous solution. The color of the detector solution H-4 can be visually confirmed. The formed detector solution does not contain glycerin as a humectant. Ozone detecting device H-4 is formed in the same manner as described above by using detector solution H-4. The color of ozone detecting device H-4 thus formed is rose pink.

Also, 0.058 g of New Coccine are dissolved in 25 ml of an aqueous 0.1-mol/liter sodium hydroxide solution, and 10 g of glycerin as a humectant and water are added to the solution to make 50 g, thereby forming detector solution I-4. Ozone detecting device I-4 is formed by using detector solution I-4 in the same manner as described above. The color of ozone detecting device I-4 thus formed is rose pink.

Furthermore, detector solution J-4 is formed by adding water to 0.058 g of New Coccine, 3.0 g of citric acid, and 10 g of glycerin as a humectant such that the total amount is 50 g, and ozone detecting device J-4 is formed by using detector solution J-4 in the same manner as described above. The color of ozone detecting device J-4 thus formed is rose pink. Ozone detecting device J-4 is a sample acidified by adding citric acid.

Each of the samples (ozone detecting devices H-4, I-4, and J-4) described above was left to stand for 5 hrs in a box filled with air in which the ozone concentration is 0.1 ppm at 25° C. and a humidity of 60%, thereby conducting an ozone gas exposure test. The color change as a result of the test was checked by measuring the reflectance of the ozone detecting device at a wavelength of 525 nm. Since the maximum portion of the spectrum of New Coccine includes 525 nm even in an acidic state, the reflectance of ozone detecting device J-4 was also measured at a wavelength of 525 nm. Note that the volume of the box is 200 liters, and, in order to analyze the internal ozone concentration, the internal air is exhausted at a rate of 2 liters/min, and air containing ozone at a predetermined concentration is supplied at a rate of 2 liters/min. Each ozone detecting device is thus exposed to the air as a detection object, and the color change of the device is measured. The color change is also visually observed. Table 16 below shows the test results.

TABLE 16

| | New Coccine | | |
|---|---|---|---|
| | H-4 | I-4 | J-4 |
| Glycerin concentration (%) | 0 | 20 | 20 |
| 0.1 ppm × 5 hrs discoloration properties | 0.00 | 0.02 | 0.00 |
| Visual confirmation | Impossible | Impossible | Impossible |

The results shown in Table 16 reveal that no discoloration by ozone was found in any detecting device. When using New Coccine, therefore, no ozone can be detected not only in an acidic state but also in an alkaline state. New Coccine is also an azo dye having an $SO_3$ group adjacently bonded to an azo group. When an azo dye has an $SO_3$ group adjacently bonded to an azo group as described above, ozone probably hardly reacts owing to steric hindrance.

From the foregoing, an azo dye having an $SO_3$ group adjacently bonded to an azo group cannot be used to detect ozone even though the dye has a hydroxy group. Also, ozone detection requires an azo dye having an $SO_3$ group bonded to a position not adjacent to an azo group, and at least one hydroxy group bonded to a position adjacent to the azo group or the p-position. Of these azo dyes, an azo dye having two hydroxy groups adjacently bonded to an azo group on different sides of the azo group can be used to detect ozone without being alkalized, provided that the dye is not acidified. In addition, alkalized azo dyes can also be used to detect ozone.

Azo dyes capable of detecting ozone when alkalized are presumably able to detect ozone because the reaction with ozone is accelerated for the following reason. That is, when these azo dyes are alkalized, an —$O^-$ group formed by eliminating hydrogen from the hydroxy group is bonded to a benzene ring or naphthalene ring bonded to an azo group, and ozone is readily entrapped in (attracted to) the —$O^-$ group. The azo dye in which ozone is thus entrapped causes the color change (discoloration) described above probably because the entrapped ozone decomposes the benzene ring (naphthalene ring) to change the dye molecular structure and electron state, and this changes light absorption in the visible region, thereby changing the color (hue).

In an acidic state, however, in which no hydrogen is released from a hydroxy group bonded to a benzene ring or naphthalene ring, the reaction with ozone does not (easily) progress. Also, in not an alkaline state but a neutral state, some azo dyes react with ozone, and a color change (discoloration) is detected. This is so presumably because a hydrogen bond is produced between hydrogen of a hydroxy group bonded to a benzene ring or naphthalene ring bonded to an azo group and nitrogen of the azo group, and oxygen of the hydroxy group becomes a δ-state that is close to the state of an —O⁻ group. Also, some hydrogen atoms are probably released even in a neutral state in some cases.

Note that a gas to be measured is not forcedly passed through the ozone detecting device in the above description, but a gas to be measured may also be forcedly passed through the ozone detecting device by using a pump or the like. This makes it possible to measure the cumulative amount of ozone within a shorter time period. Furthermore, the ozone detecting device can also be used as an ozone detecting seal by coating any surface of the device with an adhesive.

Although filter paper is used in the above description, the present invention is not limited to this. Any sheet-like paper made of cellulose fibers such as plain paper can be used as the carrier. It is also possible to use a sheet-like material (e.g., nonwoven fabric) made of fibers such as nylon or polyester, instead of cellulose, as the carrier. The carrier is preferably white, but the color of the carrier is not limited to white. Another color may also be used as long as the color change of the carrier dyed by an azo dye such Orange I or an anthraquinone-based dye such as alizarin can be confirmed.

Furthermore, sodium hydroxide is used as an alkaline substance that alkalizes an aqueous solution in the above description, but the present invention is not limited to this. For example, it is also possible to use a base, e.g., a hydroxide of an alkali metal such as potassium hydroxide, or a hydroxide of an alkali earth metal such as calcium hydroxide. In addition, even a salt can be used. That is, an alkaline substance such as sodium bicarbonate that alkalizes an aqueous solution when dissolved can alkalize (an aqueous solution of) an azo dye having a hydroxy group such as Orange I. Similarly, an alkaline substance such as sodium bicarbonate that alkalizes an aqueous solution when dissolved can alkalize an anthraquinone-based dye having a hydroxy group such as alizarin.

INDUSTRIAL APPLICABILITY

The present invention is preferably used in ozone detection.

The invention claimed is:

1. An ozone detecting device at least comprising: a carrier made of fibers;
   a dye carried by said carrier; and
   an alkaline substance carried by said carrier,
   wherein said dye is selected from the group consisting of an anthraquinone-based dye having a hydroxy group, and an azo dye having a hydroxy group and a sulfurous acid group bonded to a position not adjacent to an azo group, and
   said alkaline substance is a substance which alkalizes an aqueous solution when dissolved.

2. An ozone detecting device according to claim 1, wherein said azo dye is selected from the group consisting of Orange I, Orange II, Crocein Orange G, Tropaeolin O, Acid Alizarin Violet N, Mordant Blue 13, and calcon.

3. An ozone detecting device according to claim 1, wherein said azo dye has two hydroxy groups adjacently bonded to the azo group on different sides of the azo group.

4. An ozone detecting device according to claim 3, wherein said azo dye is selected from the group consisting of Acid Alizarin Violet N, Mordant Blue 13, and calcon.

5. An ozone detecting device according to claim 1, wherein said dye is one of alizarin and Alizarin Red S.

6. An ozone detecting device according to claim 1, wherein said alkaline substance is sodium hydroxide.

7. An ozone detecting device according to claim 1, wherein the ozone detecting device is formed by dipping said carrier in a detector solution prepared by dissolving said dye and alkalized by dissolving said alkaline substance, such that said carrier is impregnated with the detector solution, and drying said carrier.

8. An ozone detecting device according to claim 1, wherein said carrier contains a humectant carried together with said dye.

9. An ozone detecting device according to claim 8, wherein said humectant is at least one of glycerin, ethyleneglycol, and propyleneglycol.

10. An ozone detecting device according to claim 1, wherein said carrier is formed into a sheet-like shape.

* * * * *